| (12) | United States Patent | (10) | Patent No.: | US 11,058,382 B2 |
|---|---|---|---|---|
| | Hekmatshoartabari | (45) | Date of Patent: | Jul. 13, 2021 |

(54) CHARGE AMPLIFIERS THAT CAN BE IMPLEMENTED IN THIN FILM AND ARE USEFUL FOR IMAGING SYSTEMS SUCH AS DIGITAL BREAST TOMOSYNTHESIS WITH REDUCED X-RAY EXPOSURE

(71) Applicant: International Business Machines Corporation, Armonk, NY (US)

(72) Inventor: Bahman Hekmatshoartabari, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 6 days.

(21) Appl. No.: 16/733,973

(22) Filed: Jan. 3, 2020

(65) Prior Publication Data

US 2020/0138393 A1    May 7, 2020

Related U.S. Application Data

(63) Continuation of application No. 15/928,389, filed on Mar. 22, 2018.

(51) Int. Cl.
*A61B 6/00* (2006.01)
*H03F 3/193* (2006.01)
(Continued)

(52) U.S. Cl.
CPC .............. *A61B 6/502* (2013.01); *A61B 6/025* (2013.01); *A61B 6/4021* (2013.01);
(Continued)

(58) Field of Classification Search
CPC ....... A61B 6/025; A61B 6/4021; A61B 6/502; G01T 1/2018; H03F 2200/261;
(Continued)

(56) References Cited

U.S. PATENT DOCUMENTS

| 7,006,598 B2 | 2/2006 | Morii et al. |
|---|---|---|
| 7,593,508 B2 | 9/2009 | Tsuchiya |

(Continued)

FOREIGN PATENT DOCUMENTS

WO    2010046982 A1    4/2010

OTHER PUBLICATIONS

N. Wyrsch and C. Ballif "Review of Amorphous Silicon Based Particle Detectors: The Quest for Single Particle Detection" Sep. 19, 2016 [http://iopscience.iop/article/10.1088/0268-1242-31-10-103005/pdf.

(Continued)

*Primary Examiner* — Dani Fox
(74) *Attorney, Agent, or Firm* — Harrington & Smith

(57) ABSTRACT

An apparatus (e.g., an imaging system) includes a circuit, including: a p-i-n diode having a cathode coupled to a cathode bias voltage or ground; a charge transistor having a first source/drain terminal coupled to an anode of the diode; a storage capacitor having a first terminal coupled to a second source/drain terminal of the charge transistor and a second terminal coupled to the cathode; an amplification transistor having a gate terminal coupled to the first terminal of the storage capacitor and a first source/drain terminal coupled to a reference voltage; a read transistor having a first source/drain terminal coupled to a second source/drain terminal of the amplification transistor; a data line having a first terminal coupled to a second source/drain terminal of the read transistor; and a readout circuit coupled to a second terminal of the data line, providing an output voltage corresponding to charge on the storage capacitor.

9 Claims, 11 Drawing Sheets

(51) Int. Cl.
| | |
|---|---|
| *H03F 3/70* | (2006.01) |
| *A61B 6/02* | (2006.01) |
| *G01T 1/20* | (2006.01) |
| *H03F 3/45* | (2006.01) |

(52) U.S. Cl.
CPC .......... *G01T 1/2018* (2013.01); *H03F 3/193* (2013.01); *H03F 3/70* (2013.01); *H03F 3/45475* (2013.01); *H03F 2200/261* (2013.01); *H03F 2203/45514* (2013.01)

(58) Field of Classification Search
CPC ........... H03F 2203/45514; H03F 3/193; H03F 3/45475; H03F 3/70
See application file for complete search history.

(56) References Cited

U.S. PATENT DOCUMENTS

| | | |
|---|---|---|
| 8,461,545 B2 | 6/2013 | Imai |
| 9,006,635 B2 | 4/2015 | Kurokawa et al. |
| 9,063,012 B2 | 6/2015 | Thorne |
| 9,360,565 B2 | 6/2016 | Clark et al. |
| 2002/0190215 A1 | 12/2002 | Tashiro |
| 2012/0104267 A1 | 5/2012 | Matsumoto |
| 2012/0241628 A1 | 9/2012 | Hesser et al. |
| 2014/0191218 A1 | 7/2014 | Katz et al. |
| 2017/0322321 A1 | 11/2017 | Weedon et al. |

OTHER PUBLICATIONS

Feng and Sechopoulos, "Clinical Digital Breast Tomosynthesis system: Dosimetric Characterization", Radiology: vol. 263: No. 1, pp. 36-42 (Apr. 2012).
Ren, et al. A new generation FFDM/tomosynthesis fusion system with selenium detector, SPIE 2010; 7622:76220B-76211. [retrieved on Feb. 26, 2018].
Zhao and Kanicki, "Amorphous In—Ga—Zn—O thin-film transistor active pixel sensor x-ray imager for digital breast tomosynthesis", Medical Physics: vol. 41: No. 9, pp. 0919021-14 (Apr. 2014).
Stannowski, et al., "The influence of deeply-trapped charge on the transient photocurrent response of a-Si:H solar cells", Journal of Non-crystalline Solids: vol. 227-230: Part 2, pp. 1295-1299 (May 1998).
K.S. Karim, A. Nathan, and J.A. Rowlands "Alternate Pixel Architectures for Large Area Medical Imaging" University of Waterloo, Department of Electrical and Computer Engineering, Waterloo Ontartio, Canada [Downloaded from: http://proceedings.spiedigitallibrary.org on Jul. 29, 2017].
Karim S. Karim, Arokia Nathan, John Alan Rowlands "Amorphous Silicon Active Pixal Sensor Readout Circuit for Digital Imaging" IEEE Transactions on Electron Devices, vol. 50. No. 1 Jan. 2003.
"Armorphous InSnZnO Thin-Film Transistor Voltage-Mode Active Pixel Sensor Circuits for Indirect X-Ray Imagers", IEEE Transactions on Electron Devices, vol. 63, No. 12, Decmeber 2016, pp. 4802-4810 to Cheng et al. (Year: 2016).

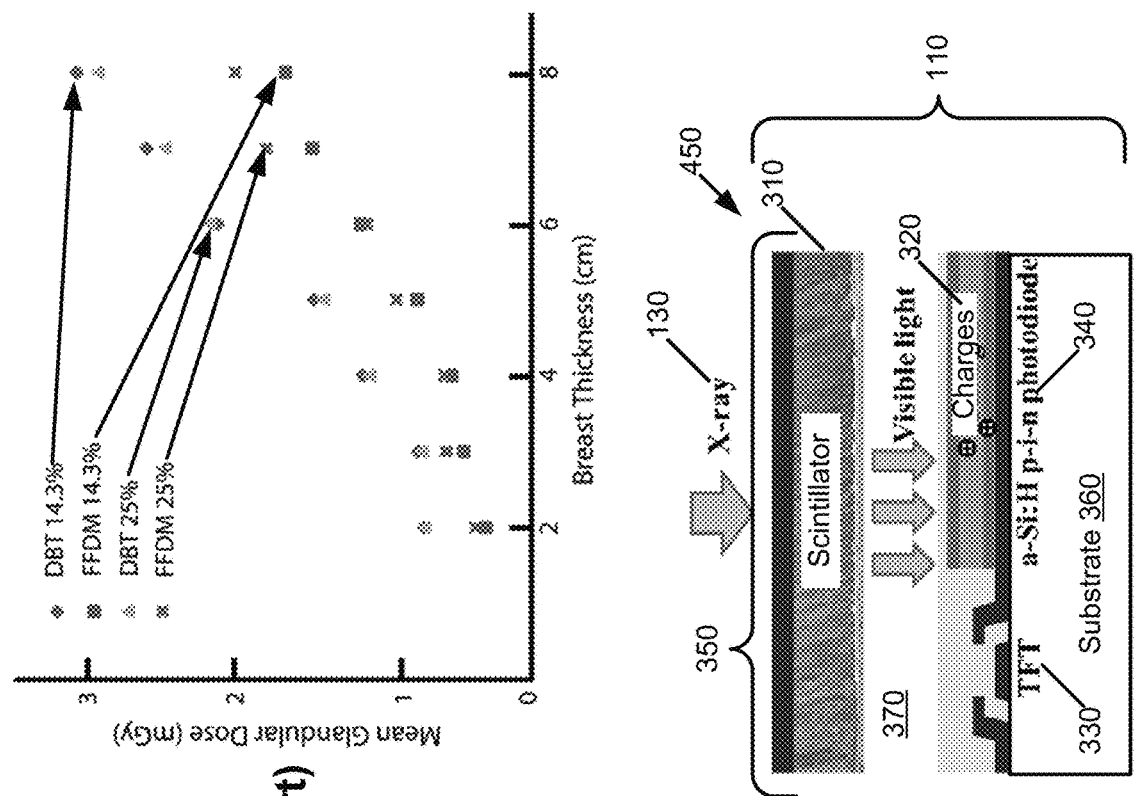
FIG. 2
(Prior Art)
FIG. 3
(Prior Art)
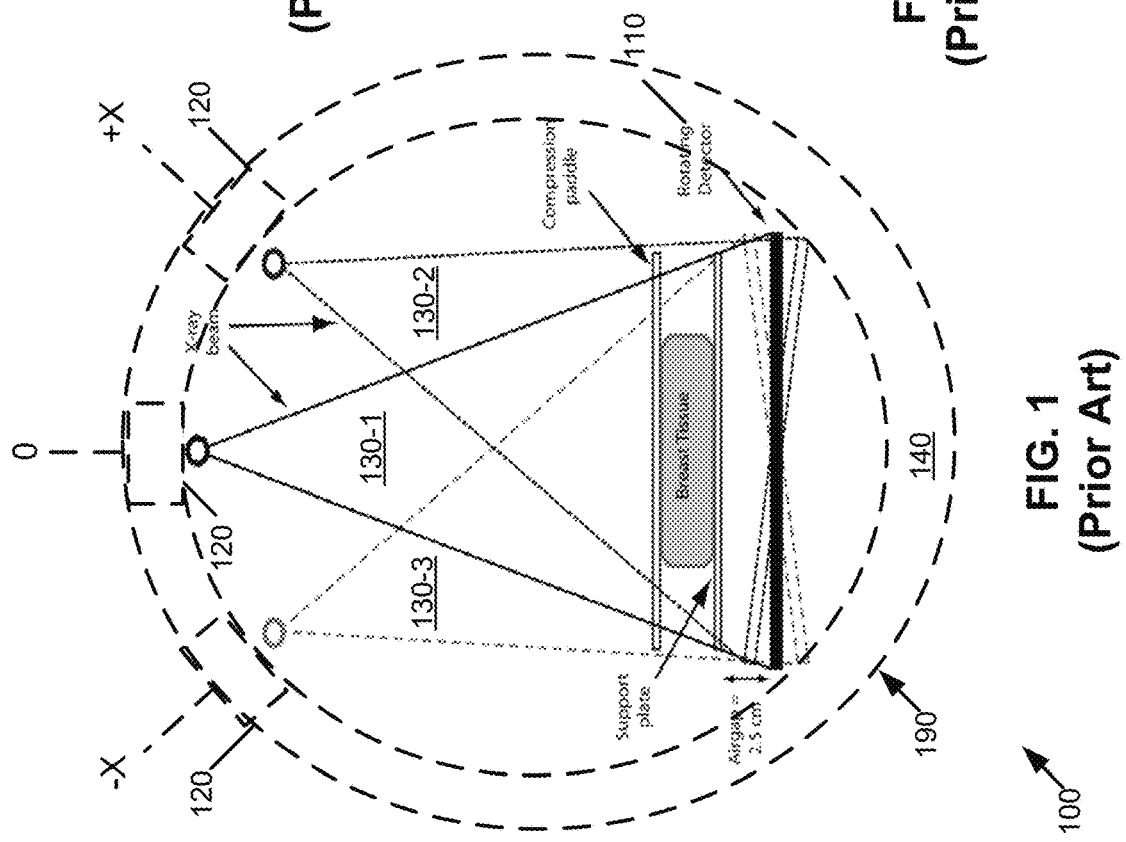
FIG. 1
(Prior Art)

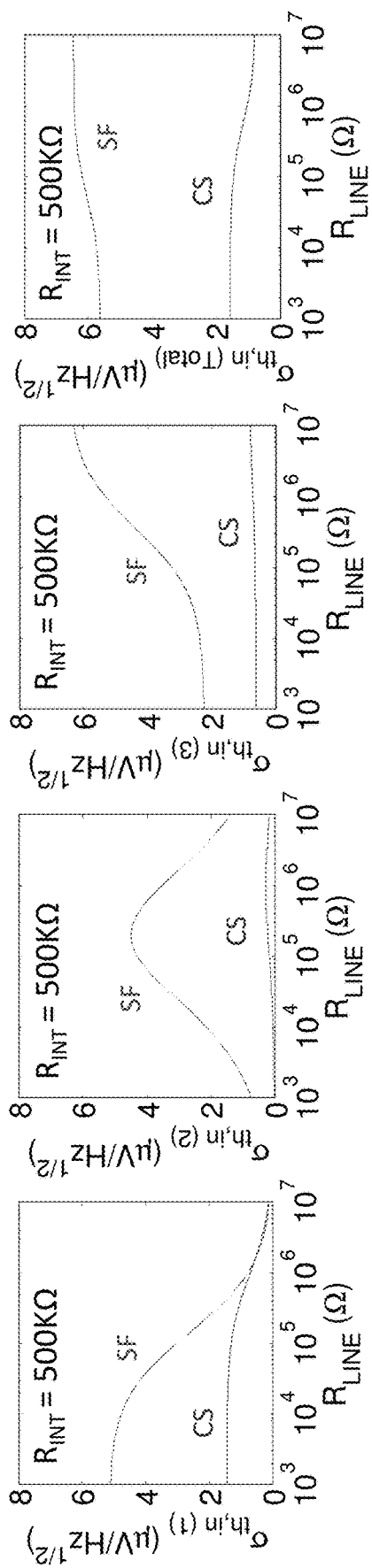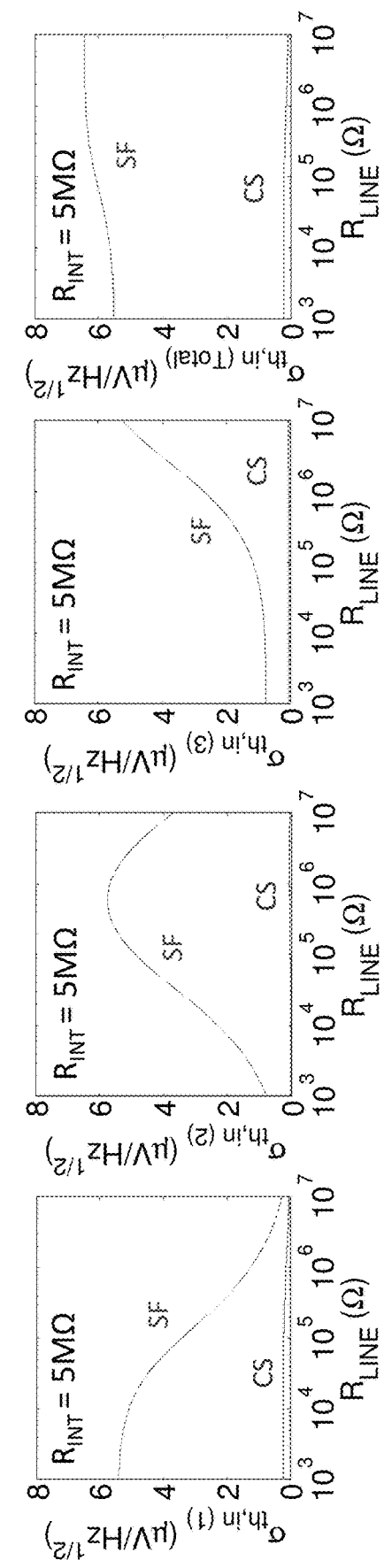
FIG. 15A  FIG. 15B  FIG. 15C  FIG. 15D
FIG. 16A  FIG. 16B  FIG. 16C  FIG. 16D

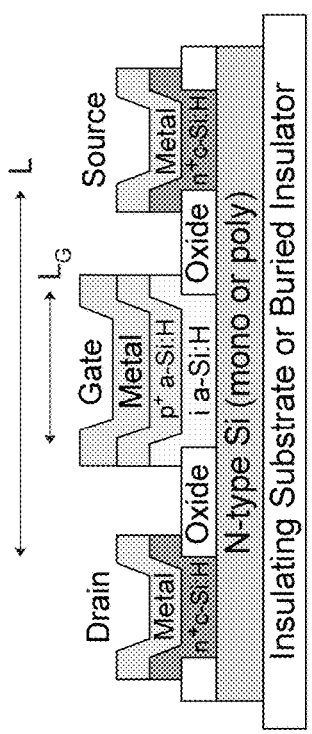
FIG. 18A
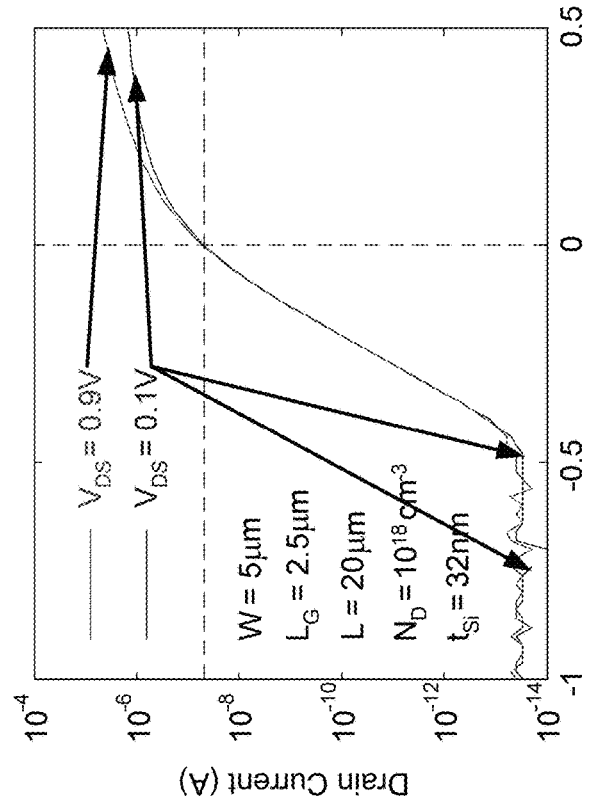
FIG. 18B
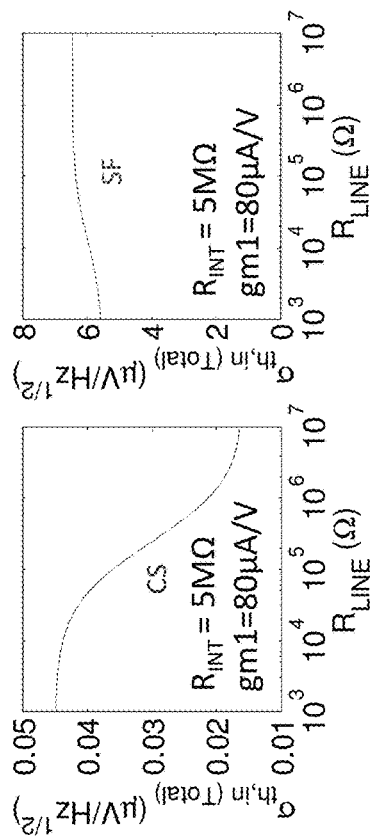
FIG. 16F
FIG. 16E
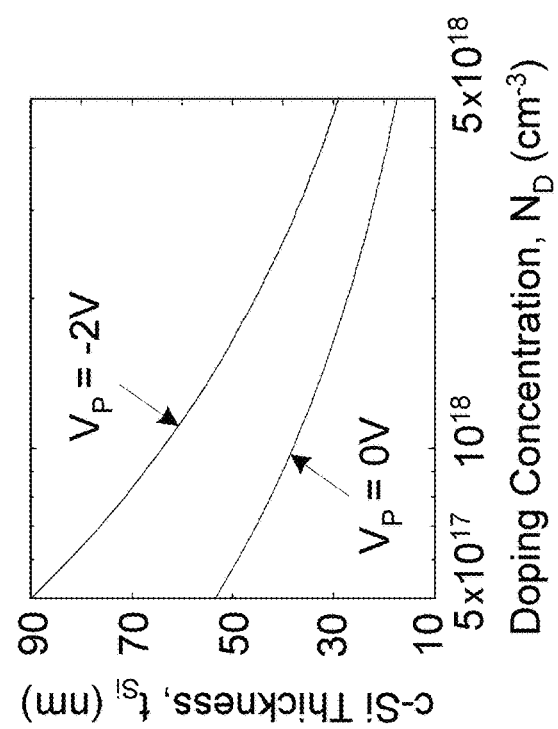
FIG. 18C

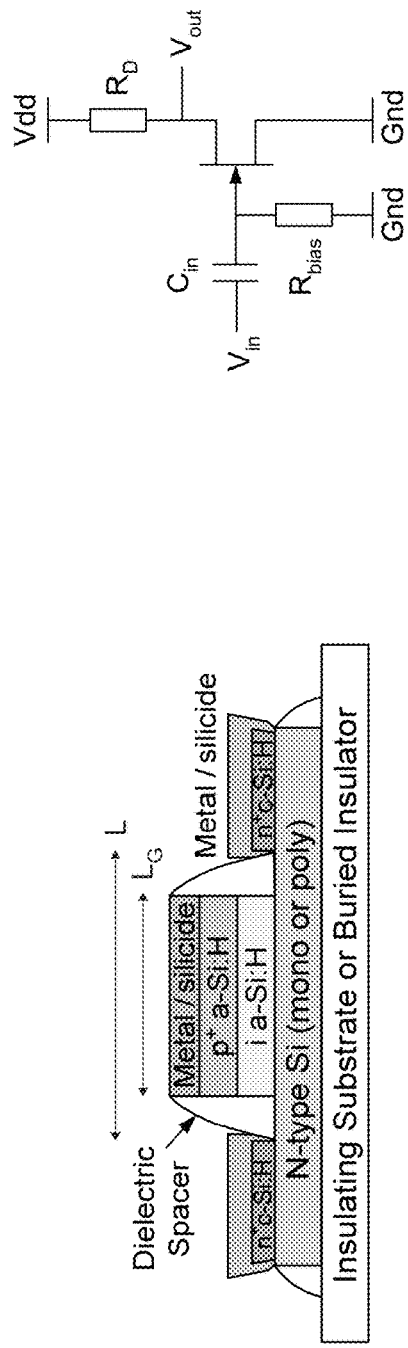
FIG. 19
FIG. 20
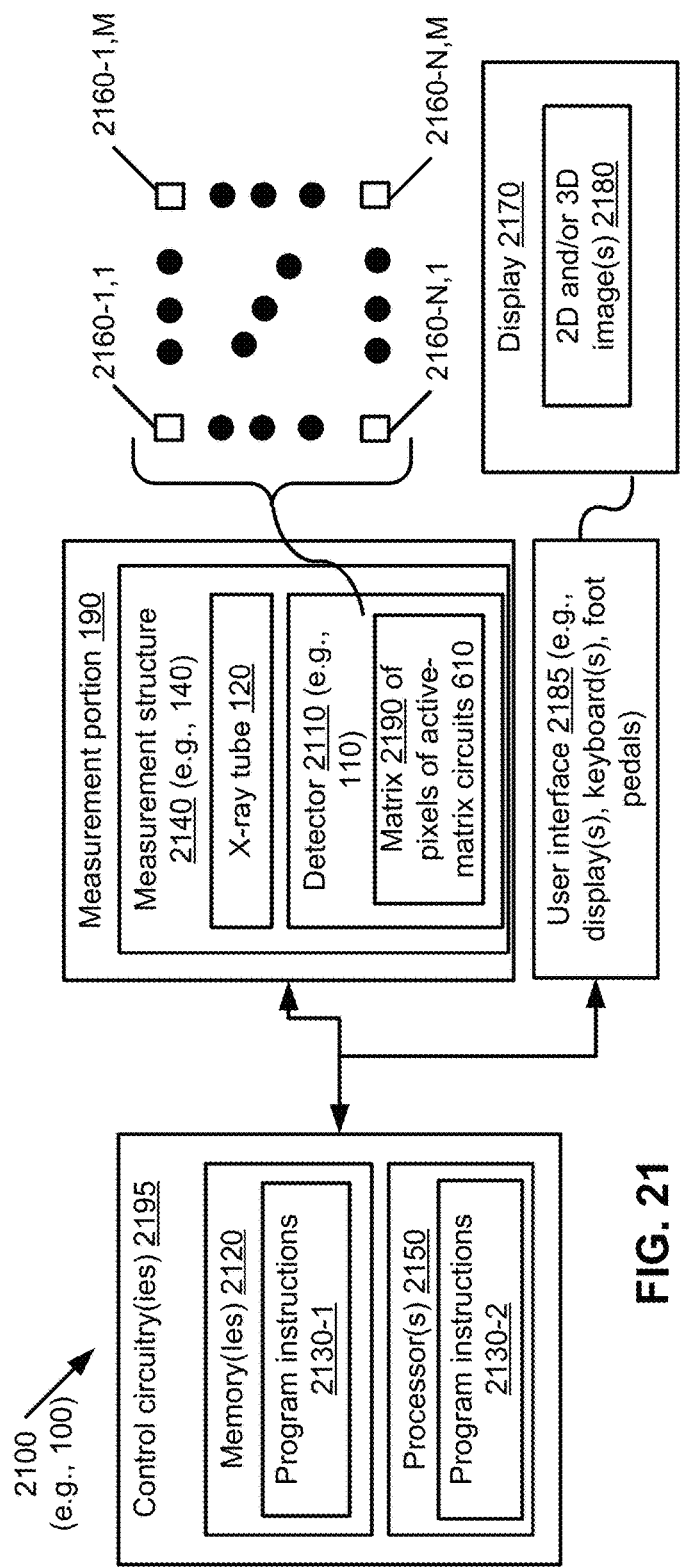
FIG. 21

US 11,058,382 B2

CHARGE AMPLIFIERS THAT CAN BE IMPLEMENTED IN THIN FILM AND ARE USEFUL FOR IMAGING SYSTEMS SUCH AS DIGITAL BREAST TOMOSYNTHESIS WITH REDUCED X-RAY EXPOSURE

CROSS-REFERENCE TO RELATED APPLICATIONS

This application is a continuation of U.S. patent Ser. No. 15/928,389, filed on Mar. 22, 2018, the disclosure of which is hereby incorporated by reference in its entirety.

BACKGROUND

This invention relates generally to amplifiers, and, more specifically, relates to charge amplifiers that can be implemented in thin film and are useful for imaging systems such as digital breast tomosynthesis with reduced X-ray exposure.

Abbreviations that may be found in the specification and/or the drawing figures are defined below, after the main part of the detailed description section.

Breast cancer is responsible for over 40,000 deaths in the U.S. annually and there are currently over 3 million U.S. women living with breast cancer diagnosis. Regular screening can reduce mortality by nearly 50 percent. In order to reduce the adverse effects of X-ray exposure, it is pertinent to minimize the X-ray exposure time during screening. With current digital breast tomosynthesis (DBT) systems, the average exposure dose received during a single screening is equal to exposure from natural sources in a span of approximately two weeks. While such exposure doses are considered generally safe for the majority of patients, or at least have benefits far outweighing the potential harms, the X-ray imaging of thick and high density breasts remains particularly challenging within safe exposure levels, often leading to under-detection, false positive results, unnecessary biopsies and other invasive procedures. Unfortunately, patients with higher density breasts are also more likely to develop breast cancer. Over 10 percent of U.S. women are categorized as having extremely high breast density.

SUMMARY

This section is meant to be exemplary and not meant to be limiting.

In an exemplary embodiment, an apparatus comprises a circuit. The circuit comprises the following: a p-i-n diode having a cathode of the p-i-n diode coupled to a cathode bias voltage or ground; a charge transistor having a first source/drain terminal coupled to an anode of the p-i-n diode; a storage capacitor having a first terminal coupled to a second source/drain terminal of the charge transistor and a second terminal coupled to the cathode of the p-i-n diode; an amplification transistor having a gate terminal coupled to the first terminal of the storage capacitor and a first source/drain terminal coupled to a reference voltage in operation; a read transistor having a first source/drain terminal coupled to a second source/drain terminal of the amplification transistor; a data line having a first terminal coupled to a second source/drain terminal of the read transistor; and a readout circuit coupled to a second terminal of the data line and configured to provide in operation an output voltage corresponding to charge on the storage capacitor caused by interaction between the p-i-n diode and light.

In another exemplary embodiment, an imaging system is disclosed. The imaging system comprises a detector comprising a matrix of pixels, the matrix comprising N rows and M columns of pixels. Each of a plurality of the pixels comprises the following: a circuit comprising: a p-i-n diode having a cathode of the p-i-n diode is coupled to a cathode bias voltage or ground; a charge transistor having a first source/drain terminal coupled to an anode of the p-i-n diode and a second source/drain terminal to the cathode of the p-i-n diode; a storage capacitor having a first terminal coupled to a second source/drain terminal of the charge transistor and a second terminal coupled to the cathode of the p-i-n diode; an amplification transistor having a gate terminal coupled to the first terminal of the storage capacitor and a first source/drain terminal coupled to a reference voltage in operation; a read transistor having a first source/drain terminal coupled to a second source/drain terminal of the amplification transistor; a data line having a first terminal coupled to a second source/drain terminal of the read transistor; and a readout circuit coupled to a second terminal of the data line and configured to provide in operation an output voltage corresponding to charge on the storage capacitor caused by interaction between the p-i-n diode and light.

BRIEF DESCRIPTION OF THE SEVERAL VIEWS OF THE DRAWINGS

FIG. 1 is a simple diagram of a portion of a DBT system for imaging breast tissue, where the DBT system could be a Hologic Selenia Dimensions system;

FIG. 2 is a graph showing medium glandular dose (MGD) (in mGy, milligray) versus breast thickness (in cm) for an exemplary DBT system;

FIG. 3 is an example of a semiconductor realization and use of a portion of a DBT active-matrix pixel;

FIGS. 15A, 15B, 15C, and 15D are graphs of first component, second component, third component, and total input-referred thermal noise variance (in $\mu V/Hz^{1/2}$), respectively, versus resistance of the line ($K_{LINE}$) for input resistance ($R_{INT}$) of a line integrator of 500 k$\Omega$ and an amplification transistor transconductance ($gm_1$) of 16 $\mu A/V$;

FIGS. 16A, 16B, 16C, and 16D are graphs of first component, second component, third component, and total input-referred thermal noise variance (in $\mu V/Hz^{1/2}$), respectively, versus resistance of the line ($R_{LINE}$) for input resistance ($R_{INT}$) of a line integrator of 500 k$\Omega$ and an amplification transistor transconductance ($gm_1$) of 16 $\mu A/V$;

FIGS. 16E and 16F are graphs of total input-referred thermal noise variance (in $\mu V/Hz^{1/2}$) versus resistance of the line ($R_{LINE}$) for input resistance ($R_{INT}$) of a line integrator of 5 M$\Omega$ and an amplification transistor transconductance ($gm_1$) of 80 $\mu A/V$, and for CS (FIG. 16E) and SF (FIG. 16F);

FIG. 18A is a structure of an underlapped thin-film HJFET used to provide parameters for the HSPICE simulation and that may be used as transistors in the active-matrix circuit 610;

FIG. 18B is a plot of measured transfer characteristics of the thin-film HJFET of FIG. 18A for VDS of 0.1V and 0.9V on a graph of drain current (in amps, A) versus gate-to-source voltage (V);

FIG. 18C illustrates calculated contour lines for two pinch-off voltages ($V_P$=0.0V and −2.0V) as a function of thickness, $t_{Si}$ (in nm) and doping concentration, $N_D$ (in cm$^{-3}$), of a crystalline silicon (c-Si) layer of the thin-film HJFET of FIG. 18A;

FIG. 19 is a structure of a self-aligned thin-film HJFET that may be used as transistors in the active-matrix circuit 610;

FIG. 20 is a circuit diagram for a thin-film HJFET, used to illustrate one example; and FIG. 21 is a block diagram of a system for imaging, such as imaging breast tissue, in accordance with an exemplary embodiment.

DETAILED DESCRIPTION

Figures 4, 5:
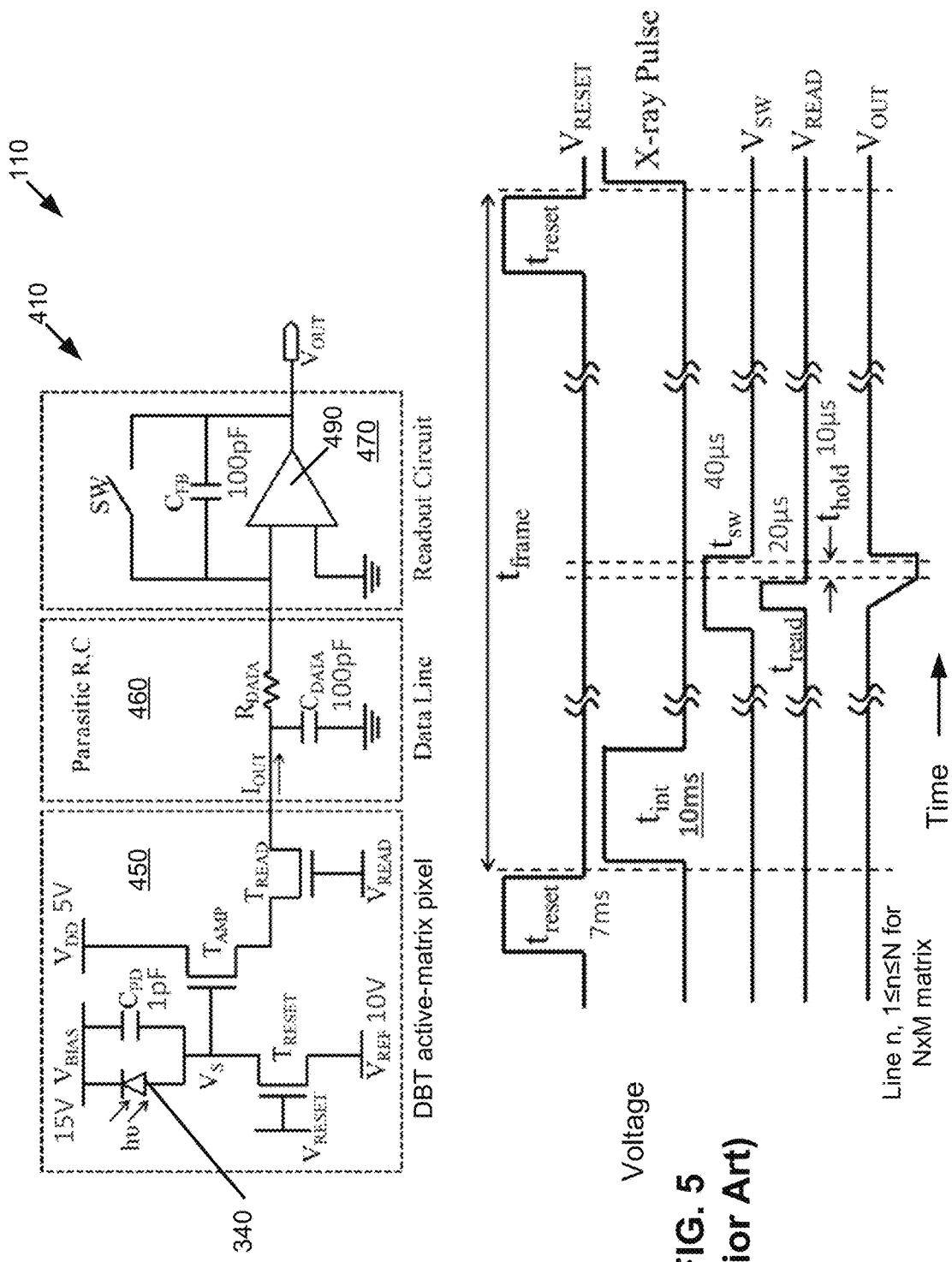
FIG. 4 is a block diagram of an active-matrix circuit.
FIG. 5 is a timing diagram of certain signals in FIG. 4 and their use with X-ray pulses to cause readout of the DBT active-matrix pixel in FIG. 4.

As stated above, the X-ray imaging of thick and high density breasts remains particularly challenging within safe exposure levels. Additional information regarding digital breast tomosynthesis (DBT) is as follows.

Turning to FIG. 1, this figure is a simple diagram of a measurement portion 190 of a DBT system 100 for imaging breast tissue, where the DBT system 100 could be a Hologic Selenia Dimensions system. This figure is a modified version of FIG. 1 from Feng and Sechopoulos, "Clinical Digital Breast Tomosynthesis system: Dosimetric Characterization", Radiology: Volume 263: Number 1, pages 36-42 (April 2012). As can be seen, an X-ray beam 130 created by an X-ray tube 120 is used to scan breast tissue placed between a compression paddle and a support plate. This example of a measurement portion 190 has a rotating detector 110, which rotates in concert with the X-ray tube 120. Both the rotating detector 110 and the X-ray tube 120 are mounted to a rotation structure 140 that provides rotation over an angular range from X degrees (e.g., −7.5 degrees) to produce X-ray beam 130-3, to and through zero (0) degrees to produce X-ray beam 130-1, and to +X degrees (e.g., +7.5 degrees) to produce X-ray beam 130-2. This system 100 can perform both 2D and 3D modeling of breast tissue. Although the rotation structure 140 is shown in a circular format, this could also be an arm or any other system allowing rotation of at least the X-ray tube 120-3 and likely the detector 110. Additionally, the exemplary embodiments herein are not limited to 3D systems and may also be applied to 2D systems.

Breast density refers to the percentage of lobules and ducts to the fatty tissue in the breast. Lobules, also known as glandular tissue, produce milk. Ducts are the vessels that carry breast milk. Breast density depends on genetics. About 10 percent of U.S. women have extremely dense breasts. FIG. 2 is a graph showing medium glandular dose (MGD) (in mGy, milligray) versus breast thickness (in cm) for an exemplary DBT system. This figure is a modified version of FIG. 3 from Feng and Sechopoulos, "Clinical Digital Breast Tomosynthesis system: Dosimetric Characterization", Radiology: Volume 263: Number 1, pages 36-42 (April 2012). Two sets of X-ray doses are plotted in the graph in FIG. 2 for breast densities of 14.3% and 25% (these percentages are glandular fractions). X-ray doses above 3 mGy exceed the safety limit set by the Mammography Quality Standards Act. Based on calculation (verified with phantom measurements), dense breasts require as high as 5 mGy for accurate imaging.

To address this issue and as an overview, we disclose a thin-film charge amplifier which can, e.g., reduce the X-ray exposure time by at least 10× (ten times). In addition, the disclosed charge amplifier and corresponding circuitry can reduce power consumption and overall image acquisition time. In some embodiments, thin-film heterojunction field-effect transistor (HJFET) devices are used for charge amplification and addressing of the active matrix detector. HJFET devices are also compatible with large-area and flexible substrates. The principles of this disclosure are also applicable to other imaging systems including full-field digital mammography (FFDM).

Now that an overview has been provided, it is helpful at this point to describe current DBT active-matrix pixels. A current DBT active-matrix pixel is illustrated using FIGS. 3, 4, and 5.

FIG. 3 illustrates an example of a semiconductor realization 350 and use of a portion of a DBT active-matrix pixel 450, as part of the detector 110. This figure is a modified version of FIG. 1(b) from Zhao and Kanicki, "Amorphous InGaZnO thin-film transistor active pixel sensor X-ray imager for digital breast tomosynthesis", Medical Physics: Volume 41: Number 9, pages 0919021-14 (April 2014). The semiconductor realization 350 as shown comprises a scintillator 310, a thin-film transistor (TFT) 330, and a diode 340 on a substrate 360. In region 370, typically a dielectric passivation layer such as oxide or nitride exists. In most cases, the TFT 330 and then the p-i-n diode 340 are fabricated, then they are passivated with the dielectric passivation layer 370 and finally the scintillator 310 is deposited on the dielectric passivation layer 370. An X-ray beam 130 illuminate a surface of the scintillator 310 and is converted to visible light using the scintillator (e.g., a-Se) and then the visible light illuminates and is detected by an a-Si:H p-i-n diode 340. As is known, a p-i-n (or PIN) diode is a diode with a wide, undoped intrinsic semiconductor region between a p-type semiconductor region and an n-type semiconductor region. The interaction between the visible light and the a-Si:H p-i-n diode 340 causes the charges 320 that are used to gauge the amount of light during readout of the DBT active-matrix pixel 450.

Referring to FIG. 4, this figure is a block diagram of an active-matrix circuit 410, and is a part of a detector 110. This figure is a modified version of FIG. 4(a) from Zhao and Kanicki, "Amorphous InGaZnO thin-film transistor active pixel sensor X-ray imager for digital breast tomosynthesis", Medical Physics: Volume 41: Number 9, pages 0919021-14 (April 2014). It is noted that the DBT active-matrix pixel may be referred to by other names, such as an active pixel sensor (APS) unit pixel. The active-matrix circuit 410 comprises the DBT active-matrix pixel 450, a data line 460, and a readout circuit 470. The p-i-n diode 340 is shown being illuminated by visible light (having an energy of E=hv, Planck's constant, h, multiplied by frequency, v). The $C_{PD}$ is internal capacitance of the p-i-n diode 340. The semiconductor realization 350 in FIG. 3 can be considered to show the p-i-n diode 340 and the amplification transistor $T_{AMP}$. The readout circuit 470 includes an operational amplifier (OpAmp) 490, a feedback capacitor ($C_{FB}$) and a switch SW. The data line 460 includes parasitic resistance $R_{DATA}$ and parasitic capacitance $C_{DATA}$. FIG. 4 also illustrates possible values for some of the elements: $V_{BIAS}$ may be 15 volts (V); $C_{PD}$ may be 1 pF; $V_{REF}$ may be 10V; $V_{DD}$ may be 5V; $C_{DATA}$ may be 100 pF; and $C_{FB}$ may be 100 pF.

FIG. 5 is a timing diagram of signals in FIG. 4 and their use with X-ray pulses to cause readout of the DBT active-matrix pixel in FIG. 4. This figure is a modified version of FIG. 4(b) from Zhao and Kanicki, "Amorphous In—Ga—Zn—O thin-film transistor active pixel sensor X-ray imager for digital breast tomosynthesis", Medical Physics: Volume e 41: Number 9, pages 0919021-14 (April 2014). Examples of possible timing periods are also reset illustrated: $t_{reset}$ may be 7 ms; $t_{int}$ for the X-ray pulse may be 10 ms; the $t_{sw}$ may be 40 µs; $t_{read}$ may be 20 µs; and $t_{hold}$ may be 10 µs. The output voltage, $V_{OUT}$, is for line n, $1 \leq n \leq N$ for an N×M matrix (N rows by M columns).

One issue with this implementation is that X-ray exposure time ($t_{int}$) is high (e.g., 10 ms), primarily because X-ray-to-visible conversion efficiency is limited, resulting in low optical current ($I_{opt}$). For example, an implementation with the following parameters: $I_{opt}$=0.5 nA, $C_{PD}$=1 pF, $V_{bias}$−$V_{REF}$=5V, results in $t_{int}$=5V×1 pF/0.5 nA=10 ms.

Other issues include the following. In order to keep the effective photodetector capacitor ($C_{PD,eff}$) low, a source-follower circuit with a voltage gain $A_V \approx 1$ is used. Note $C_{PD,eff}=C_{PD}+(1-A_V) C_{gs,AMP}$, where $C_{PD}$ is approximately the capacitance of the i-layer in the p-i-n diode, and the term $(1-A_V)C_{gs,AMP}$ is due to Miller effect.

Since a source-follower is used, large $I_{out}$ is required to (i) suppress effect of parasitic R, and ON resistance of $T_{READ}$ and (ii) reduce noise. Therefore large W/L ratios are needed for both $T_{AMP}$ and $T_{READ}$ limiting pixel resolution. As it is known, if double-sampling is used to eliminate flicker noise, other sources of noise (e.g., thermal noise+reset noise+amplifier noise) are doubled. Therefore, double-sampling alone does not address the resolution issue.

Figures 6, 7:
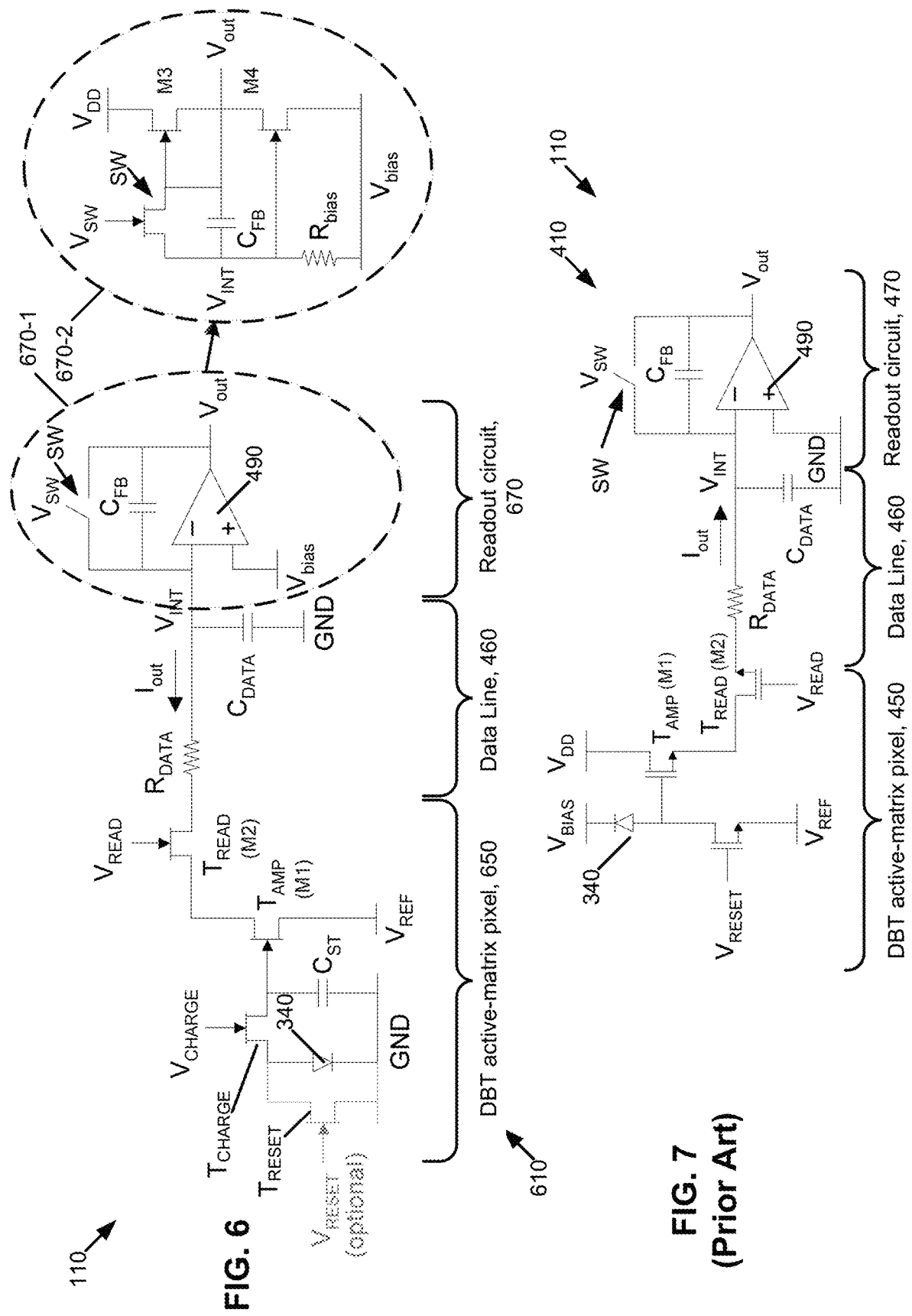
FIG. 6 is a block diagram of an active-matrix circuit in accordance with exemplary embodiments, and is a part of a detector 110.
FIG. 7 illustrates an active-matrix circuit in block diagram form and is another view of FIG. 4.

Turning to FIG. 6, this figure is a block diagram of an active-matrix circuit 610 in accordance with exemplary embodiments. The active-matrix circuit 610 is part of a detector 110. The active-matrix circuit 610 can be thought to comprise the DBT active-matrix pixel 650, the data line 460, and the readout circuit 670. The p-i-n diode 340 is part of the pixel 650, which also comprises a charge transistor, $T_{CHARGE}$, an amplification transistor, $T_{AMP}$ (also shown as M1), a read transistor, $T_{READ}$ (also shown as M2), and a storage capacitor, $C_{ST}$. References 670-1 and 670-2 indicate two possible readout circuits 670. The data line 460 comprises a parasitic resistance, $R_{READ}$, and a parasitic capacitance, $C_{DATA}$. Two readout circuits 670-1, 670-2 are shown. The $V_{INT}$ is the voltage at an "input" to an integrator, and the readout circuit 670 may also be referred to as an integrator. The Readout circuit 670-1 comprises an OpAmp 490, a switch SW responsive to a voltage $V_{SW}$, and a feedback (FB) capacitor, $C_{FB}$. Readout circuit 670-2 comprises a switch, SW (a transistor in this example), that is responsive to the voltage $V_{SW}$, a feedback capacitor, $C_{FB}$, a bias resistor, $R_{bias}$, and two transistors M3 and M4. Each of the transistors shown in FIG. 6 includes two source/drain terminals and a gate terminal. The $V_{bias}$ is a bias voltage, the $V_{REF}$ is a reference voltage, and $V_{DD}$ is a (e.g., drain) supply voltage.

The multiple transistor (M3, M4) circuit in readout circuit 670-2 is an OpAmp circuit implemented with, e.g., thin-film transistors M3, M4. In this exemplary circuit, M4 is an amplification transistor operative as a common-source amplifier, and M3 is an active load formed by connecting the gate terminal of M3 to its source terminal. Such an implementation is feasible for HJFET and depletion-mode MOSFET given that the transistor may operate in saturation (in subthreshold or above threshold) at a gate-to-source voltage of zero and therefore function as a substantially constant current source with a high output resistance. As known in the art, an active load may also be formed by connecting the gate of M3 to a gate bias voltage. Other known configurations including a diode-connected transistor (with gate terminal connected to drain terminal) and a passive load (resistor) may also be used. The readout circuit 670-2 is one possible circuit implementation for the OpAmp 490 of the readout circuit 670-1. Other circuits known for implementing OpAmps including cascaded (multi-stage), cascode and differential circuits could also be used. In conventional designs, instead of using thin-film transistors (TFTs) to fabricate the OpAmp circuit monolithically, typically a CMOS IC (which is fabricated separately) is used as an OpAmp 490 and this IC is mounted on the thin-film transistor panel, e.g., with bonding. OpAmps implemented with CMOS likely have higher performance than OpAmps implemented with TFTs because CMOS transistors have higher performance than TFTs. But for the disclosed circuit 610, the performance of the OpAmp implemented with TFTs M3 and M4 is adequate, for reasons explained below. Therefore externally mounted ICs are not required to implement the OpAmps, but they may be used in some embodiments and are within the scope of this invention.

FIG. 7 illustrates an active-matrix circuit 410 in block diagram form and is another view of FIG. 4. The amplification transistor, $T_{AMP}$, is also referred to as M1, and the read transistor, $T_{READ}$, is referred to as M2. The switch SW is responsive to a voltage, $V_{SW}$. This figure is for ease of reference, as many comparisons between FIGS. 6 and 7 will be made in the following description.

Comparing FIGS. 6 and 7, with reference to readout circuit 670-1 of FIG. 6 also, the OpAmp 490 in FIG. 7 has its non-inverting input (+) connected to ground (GND) and its inverting input (−) is coupled to an output terminal of the data line 460 (and to terminals of the feedback capacitor and the switch). Meanwhile, in OpAmp 490 in readout circuit 670-1 of FIG. 6, the non-inverting input (+) is connected to $V_{bias}$ and the inverting input (−) is coupled to an output terminal of the data line 460 (and to terminals of the feedback capacitor and the switch). Note, as it is customary in the field of electrical circuits, GND does not necessarily refer to the global ground and it may refer to a local ground or a reference ground as well.

In the disclosed structure of FIG. 6, $V_{bias}$, (the bias voltage of the non-inverting input node of the OpAmp 490) is larger than $V_{REF}$ (reference voltage connected to the source of $T_{AMP}$), therefore current $I_{out}$ flows from the OpAmp 670 towards $T_{AMP}$ as shown, and the source/drain terminal of $T_{AMP}$ which is connected to $T_{READ}$ is the functional drain of $T_{AMP}$. As a result, $T_{AMP}$ is configured as a common-source (CS) amplifier. In conventional designs such as in FIG. 7, $T_{AMP}$ is connected to $V_{DD}$ and the non-inverting input to the OpAmp 490 is grounded (i.e., connected to GND) and $V_{DD}$ is larger than GND, so $I_{out}$ flows in the direction shown in FIG. 7 (towards the OpAmp 490), and therefore the source/drain terminal of $T_{AMP}$ which is connected to $T_{READ}$ is the functional source of $T_{AMP}$. As a result, $T_{AMP}$ is configured as a source-follower (SF) amplifier. As will be discussed later, a CS amplifier configuration increases the voltage gain and therefore reduces the input-referred noise compared to that of a SF amplifier configuration and therefore preferred in some embodiments. However, SF amplifier configuration may also be used in some embodiments and is within the scope of this invention.

While the transistors used in the exemplary drawing of FIG. 6 are HJFETs, it will be appreciated that other types of transistors such as MOSFETs (depletion-mode or enhancement mode), may also be used. Also, while the transistors used in the exemplary drawing of FIG. 6 (and also FIG. 7) are n-channel transistors, it will be appreciated that p-channel transistors may also be used (with necessary adjustments in biasing and voltage levels as apparent to those skilled in the art). Other variations to the circuit of FIG. 6 as apparent to those skilled in the art may also be used. For example, the source terminal of $T_{AMP}$ may be connected to GND (instead of $V_{REF}$) and the cathode of the p-i-n diode 340 may be connected to $V_{REF}$ (instead of GND).

Figure 8:
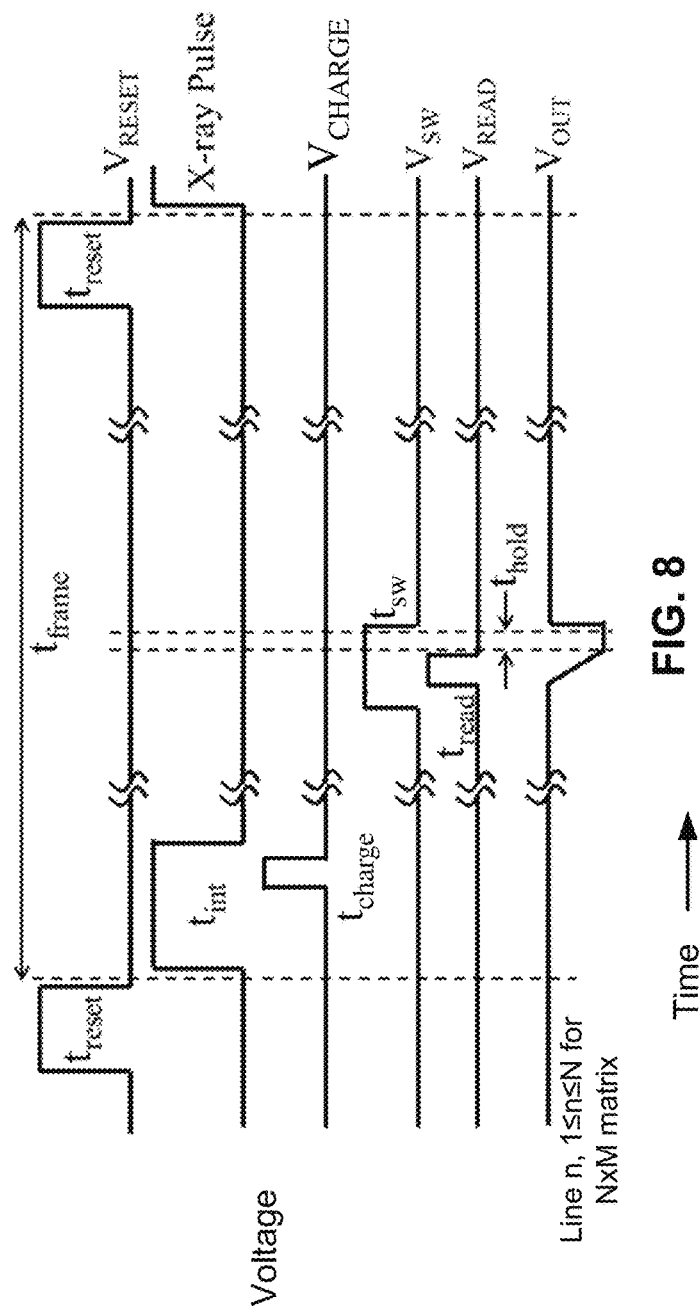
FIG. 8 is a timing diagram of certain signals in FIG. 6 and their use with X-ray pulses to cause readout of the DBT active-matrix pixel in FIG. 6.

Before describing certain possible features of FIG. 6 in relation to FIG. 7, it is helpful to describe how the circuit in FIG. 6 might be used to read out the DBT active-matrix pixel 650. FIG. 8 is a timing diagram of certain signals in FIG. 6 and their use with X-ray pulses to cause readout of the DBT active-matrix pixel in FIG. 6. The operation sequence is similar to that shown in FIG. 5, except that RESET ($t_{reset}$) is optional and CHARGE ($t_{charge}$) is performed during X-ray exposure ($t_{int}$), e.g. as shown in FIG. 8. Other variations of the operation sequence (e.g., waveform shapes, line multiplexing schemes, and the like) known in the art may also be used, with the two exceptions mentioned above. Additional details about certain of the time periods in FIG. 8 are described below.

Figure 9C:
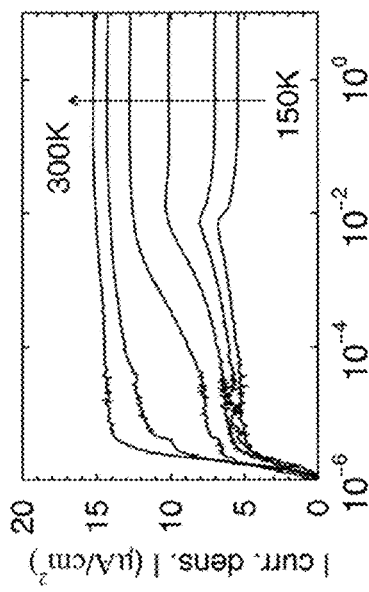
FIG. 9C is a graph of short-circuit current density (in $\mu A/cm^2$) versus illumination time (in seconds) for p-i-n diode 340 at various temperatures ranging from 150K to 300K.
Figure 9B:
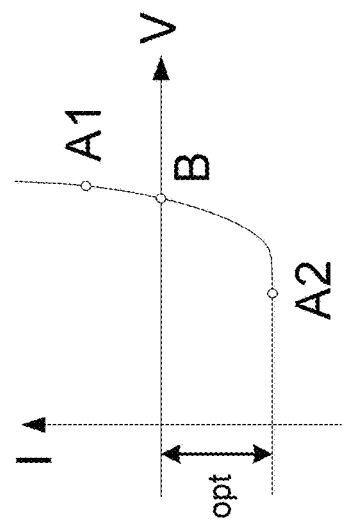
FIG. 9B illustrates a current (I)-voltage (V) graph for p-i-n diode 340 in FIG. 9A.

Referring to FIGS. 6 and 7, a first feature of the active-matrix circuit 610 is as follows. The p-i-n diode 340 in active-matrix circuit 610 operates in solar cell mode. Together with other features, this enables 10-100× lower X-ray dose. Meanwhile, the p-i-n diode 340 in FIG. 7 operates in photodetector mode (also known as photodiode mode). As background, a p-i-n diode operating in solar cell mode (as in FIG. 6), develops a photo-generated positive voltage polarity on its p-side (anode) with respect to its n-side (cathode) under illumination, and it can deliver current to an external circuit the same way as a conventional battery. In contrast, a p-i-n diode operating in photodetector mode (as in FIG. 7) is biased with a negative voltage on its p-side (anode) with respect to its n-side (cathode), resulting in flow of photo-generated current (i.e. optical current) from its n-side (cathode) to its p-side (anode) under illumination. Referring to FIG. 9B, which represents typical I-V characteristics of a p-i-n diode (such as p-i-n diode 340) under a given illumination level, the 3rd quadrant portion of the I-V curve ($V \geq 0$ and $I \leq 0$) represents the solar cell operation mode, whereas the 4th quadrant portion of the I-V curve ($V<0$ and $I<0$) represents the photodetector operation mode. The two operation points where $I=0$ and $V=0$ are commonly referred to as the open-circuit and short-circuit operation points of the solar cell.

The voltage stored on $C_{ST}$ after X-ray exposure for FIG. 6 is given by $V_{ST}=n_0(KT/q) \ln(I_{opt}/I_{dark})$, where $n_0$ is the ideality factor of the p-i-n diode, $I_{opt}$ is the optical current (photocurrent) of the p-i-n diode, $I_{dark}$ is the dark current of the p-i-n diode (i.e. reverse saturation current of the p-i-n diode under no illumination), K is the Boltzmann constant, T is the absolute temperature, q is the electron charge, and ln(•) is natural logarithm.

In contrast, the voltage stored on $C_{PD}$ (internal capacitance of the p-i-n diode, which is approximately equal to the capacitance of the i-layer) of FIG. 7 after X-ray exposure is given by: $\Delta V_{ST}=V_{ST}-(V_{BIAS}-V_{REF})=I_{opt} \times t_{int}/C_{PD}$, where $I_{opt}$ is the photocurrent, and $t_{int}$ is the X-ray exposure time.

A second feature of active-matrix circuit 610 of FIG. 6 is as follows. The readout circuit 670 is connected to the functional drain of the charge-amplification transistor, $T_{AMP}$, which provides two advantages compared to a connection to the functional source. The first advantage is enabling a higher charge gain by configuring $T_{AMP}$ as a common-source amplifier as opposed to a source-follower. The second advantage is that, so far as $T_{MAP}$ is biased in saturation (in subthreshold or above threshold), the output current $I_{out}$ is not affected by ON resistance of $T_{READ}$ and parasitic resistance of data line, $R_{DATA}$. One practical implication of this is that the requirement on $T_{READ}$ to have a large (e.g., relative) W/L (channel width to channel length ratio) to ensure a low ON-resistance is relaxed, allowing higher pixel resolution.

By contrast, for the circuit in FIG. 7, the readout circuit is connected to the functional source of the charge-amplification transistor, $T_{AMP}$, thereby limiting the charge gain. In addition, output current $I_{out}$ is reduced by ON-resistance of $T_{READ}$ and parasitic resistance of data line, $R_{DATA}$. Therefore, $T_{READ}$ needs a (e.g., relatively) large W/L, limiting the pixel resolution.

A third feature of active-matrix circuit 610 of FIG. 6 is as follows. In preferred embodiments, charge-amplification transistor $T_{AMP}$ is biased in subthreshold regime, which enables wide dynamic range. As background, subthreshold regime refers to the transistor operation regime where the gate-to-source voltage is below the pinch-off voltage of HJFET (or threshold voltage of MOSFET) but above the gate-to-source cut-off voltage. In contrast, above-threshold regime refers to the transistor operation regime where the gate-to-source voltage is above the pinch-off of voltage of HJFET (or above the threshold voltage of MOSFET). When operating in subthreshold or above threshold, the transistor may operate in a linear regime or saturation regime depending on its drain-to-source voltage. Saturation in subthreshold requires $V_{DS} \gg KT/q$ (typically $V_{DS} > 5KT/q$ is adequate) whereas saturation above threshold requires $V_{DS} > V_{GS}-V_p$ for HJFET or $V_{DS} > V_{GS}-V_T$ for MOSFET. (Note these definitions are given with respect to n-channel transistors. For p-channel transistors, the same definitions apply after reversing the voltage polarities). In the active-matrix circuit 610 of FIG. 6, the gate-to-source voltage of $T_{AMP}$ is given by $V_{GS1}=V_{ST}-V_{REF}$, therefore, operation in subthreshold requires $V_{ST}-V_{REF}<V_p$, which can be ensured by a proper choice of $V_{REF}$. Assuming that the drain-to-source voltage of $T_{AMP}$ is sufficiently larger than KT/q to ensure saturation in subthreshold (e.g. larger than 5KT/q), output current (for HJFET or MOSFET) is given by $I_{out}=I_{D0}\exp(qV_{ST}/n_1KT)$, where $n_1$ is the ideality factor of the drain current, $I_{D0}$ is the drain saturation current at $V_{GS}=-V_{REF}$ and exp(•) means exponent. As discussed earlier, $V_{ST}=n_0(KT/q)\ln(I_{opt}/I_{dark})$ therefore output current maybe expressed as $I_{out}=I_{D0}(I_{opt}/I_{dark})_{n0/n1}\approx I_{D0}\times I_{opt}/I_{dark}$. The approximation on the right-hand-side is reasonable since for well-designed diodes and transistors, $n_0$ and $n_1$ are both typically in the range of 1.1-1.4 with the range 1.2-1.3 being more typical.

Small signal transconductance of the amplification transistor, $T_{AMP}$ (M1) is as follows (for HJFET or MOSFET): $gm_1=\partial I_{out}/\partial V_{GS1}=I_{out}/[n_1KT/q]$, where $I_{D0}$ is drain current at $V_{GS1}=-V_{REF}$, $V_{DS1}>>KT/q$, GS refers to gate-to-source, and DS refers to drain-to-source and the subscript "1" refers to M1. As can be seen, the expressions derived for $gm_1$ and $I_{out}$ are both independent of the ON-resistance of $T_{READ}$ (referred to as $R_{ON2}$) and parasitic resistance of the data line, $R_{DATA}$. Note the independence of $gm_1$ and $I_{out}$ from $R_{ON2}$ and $R_{DATA}$ is the consequence of connecting $T_{READ}$ to the functional drain of $T_{AMP}$ and biasing $T_{AMP}$ is saturation; while the nearly linear dependence of $I_{out}$ on $I_{opt}$ (given by $I_{out}\approx I_{D0}\times I_{opt}/I_{dark}$) is the consequence of biasing $T_{AMP}$ in subthreshold. If $T_{AMP}$ is biased in saturation but above threshold instead of subthreshold, $I_{out}$ and $gm_1$ (for HJFET) are given by $$I_{out}=G_0V_p\left[\frac{V_{GS1}}{V_p}+\frac{2}{3}\left(-\frac{V_{GS1}}{V_p}\right)^{3/2}+\frac{1}{3}\right]\approx I_{DSS1}\left(1+\frac{V_{GS1}}{V_p}\right)^2,$$

and $$gm_1=G_0[1-(V_{GS1}/V_p)^{1/2}],$$

where $V_{GS1}=V_{ST}-V_{REF}=n_0(KT/CI)\ln(I_{opt}/I_{dark})-V_{REF}$, $G_0=(W/L)_1 qN_D\mu_n t_{Si}$, $I_{DSS1}$, is the drain saturation current of $T_{AMP}$ at $V_{GS1}=0$, $N_D$ is doping concentration in the HJFET channel, $\mu_n$ is the bulk mobility of electrons in the HJFET channel and $t_{Si}$, is the thickness of the HJFET channel material (e.g. c-Si). As can be seen, $g_{m1}$ and $I_{out}$ are still independent of $R_{ON2}$ and $R_{DATA}$ but $I_{out}$ no longer has a linear dependence on $I_{opt}$. While $T_{AMP}$ is biased in sub-threshold to ensure linearity (and also lower power consumption due to lower current levels) in preferred embodiments, it will be appreciated that in some embodiments, $T_{AMP}$ may be biased above threshold and such embodiments are within the scope of this invention. If $T_{AMP}$ is a MOSFET instead of an HJFET, the equations for $I_{out}$ and $g_{m1}$ must be adjusted as below but the same conclusions given above for HJFET apply:

$$I_{out}=\tfrac{1}{2}K_{AMP}(V_{GS1}-V_T)^2, \text{ and}$$

$$g_{m1}=K_{AMP}(V_{GS1}-V_T)$$

where $V_{GS1}=V_{ST}-V_{REF}$, $K_{AMP}=\mu_n C_i (W/L)_1$, $K_{AMP}$ is the saturation constant of $T_{AMP}$, $\mu_n$ is the field-effect electron mobility of $T_{AMP}$, $C_i$ is the gate insulator capacitance per unit area of $T_{AMP}$, and $V_T$ is the threshold voltage of $T_{AMP}$.

With respect to FIG. 7, $T_{AMP}$ is biased in saturation regime above threshold, and $gm_1$ and $I_{out}$ are given by:

$$gm_1=\frac{1}{R_{ON2}+R_{DATA}}\left[1-\frac{1}{\sqrt{1+4K_{AMP}(R_{ON2}+R_{DATA})(V_{G1}-V_T)}}\right],$$

$$I_{out}=\frac{1+2K_{AMP}(R_{ON2}+R_{DATA})(V_{G1}-V_T)-\sqrt{1+4K_{AMP}(R_{ON2}+R_{DATA})(V_{G1}-V_T)}}{2(R_{ON2}+R_{DATA})^2 K_{AMP}}.$$

In the above equations, $K_{AMP}=\mu_n C_i (W/L)_1$, $R_{ON2}=1/[\mu_n C_i (W/L)_2(V_{GS2}-V_T)]$, $V_{GS2}=V_{READ}-R_{DATA}I_{out}$, and $V_{G1}=V_{REF}+I_{opt}\times t_{int}/C_{PD}$, $R_{ON2}$ is the channel ON-resistance of $T_{READ}$, $V_T$ is the threshold voltage of $T_{AMP}$ and $T_{READ}$, and the subscripts "1" and "2" refer to M1 ($T_{AMP}$) and M2 ($T_{READ}$), respectively. The dependence of $gm_1$ and $I_{out}$ on $R_{DATA}$ and $R_{ON2}$, is evident from the above equations. In addition, $I_{out}$ does not have a linear dependence on $I_{opt}$. Therefore, the above equations indicate a narrower dynamic range as compared to that of FIG. 6.

A fourth feature of active-matrix circuit 610 of FIG. 6 is as follows. In FIG. 6 there is no need for external line integrators such as mounted CMOS chips for the OpAmp 490 of the readout circuit 670-1 (although as described above, these may be used if desired). This is because the performance requirements of a line integrator (e.g., readout circuit 670) are not stringent. A single-stage common-source amplifier implemented by thin-film transistors M2 and M3 can be used in conjunction with a feedback capacitor ($C_{FB}$) and a switching thin-film transistor (SW) to form a sufficiently high performance line integrator, as illustrated by readout circuit 670-2. If low-noise TFTs (e.g., HJFETs) are used, amplifier noise can be even lower than CMOS.

For the circuit in FIG. 7, by contrast, external line integrators such as the OpAmp 490 and the circuitry in the readout circuit 470 are needed. This is because the integrator needs high input impendence, high gain, and low noise. For a typical CMOS op-amp, the noise spectrum is given by $S_{INT}^2=S_{INT,0}^2+\delta C_{DATA}$, and $S_{INT,0}$ depends on op-amp design. Typically $\delta\approx 15$.

Figure 9A:
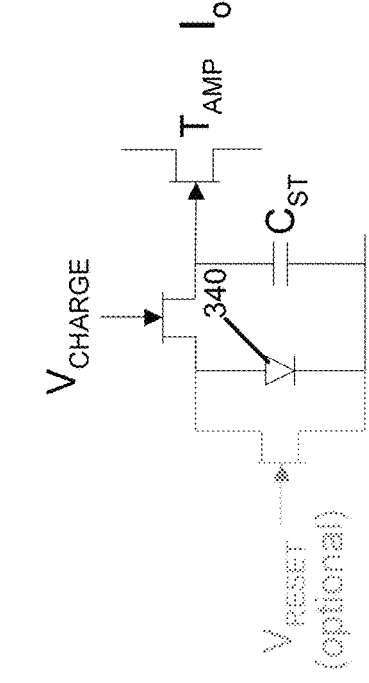
FIG. 9A illustrates a detector portion of the active-matrix circuit 610 from FIG. 6.
Figure 9D:
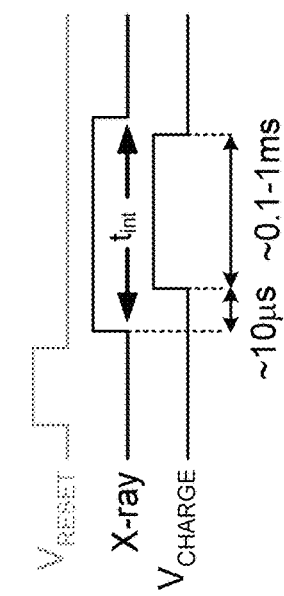
FIG. 9D is a timing diagram of certain signals in FIG. 9A.
Figure 12A:
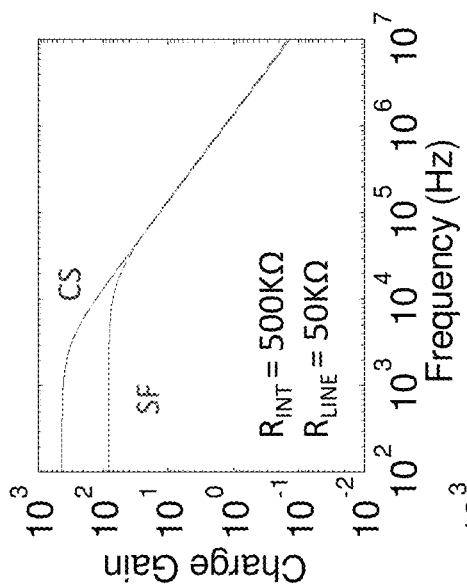
FIGS. 12A, 12B, 12C, and 12D are graphs of charge gain versus frequency for $R_{INT}=500$ k$\Omega$ and $R_{LINE}=500$ k$\Omega$ in FIG. 12A, for $R_{INT}=50$ k$\Omega$ and $R_{LINE}=500$ k$\Omega$ in FIG. 12B, for $R_{INT}=500$ k$\Omega$ and $R_{LINE}=50$ k$\Omega$ in FIG. 12C, and for $R_{INT}=50$ k$\Omega$ and $R_{LINE}=50$ k$\Omega$ in FIG. 12D.
Figure 12B:
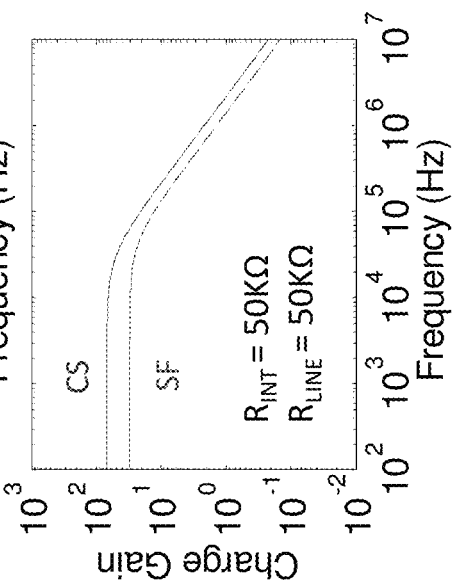
Figure 12C:
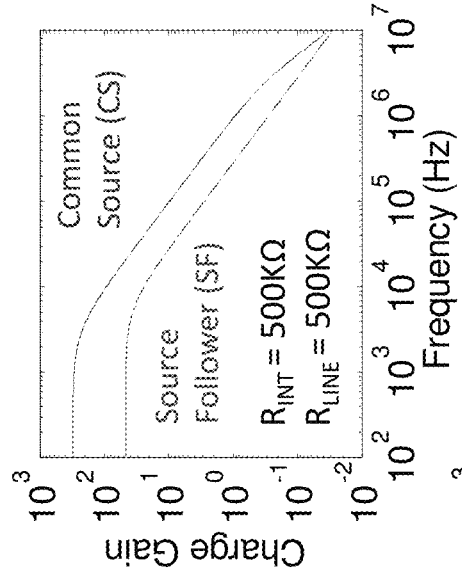
Figure 12D:
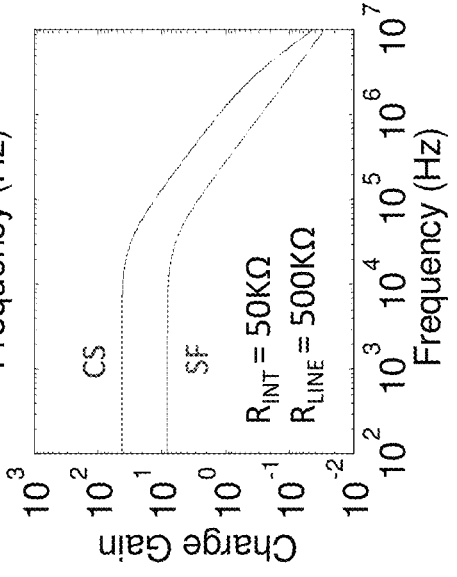

Additional details are now presented for the active-matrix circuit 610. Referring now to FIGS. 9A-9D, where FIG. 9A illustrates a detector portion of the active-matrix circuit 610 from FIG. 6, FIG. 9B illustrates a current (I)-voltage (V) characteristics graph for p-i-n diode 340 in FIG. 9A, FIG. 9C is a graph of short-circuit current density (in μA/cm²) versus illumination time (in seconds) for a p-i-n diode, such as p-i-n diode 340 in FIG. 9A, and FIG. 9D is a timing diagram of certain signals in FIG. 9A. FIG. 9C is a modified version of FIG. 1 (top) from Stannowski, et al., "The influence of deeply-trapped charge on the transient photocurrent response of a-Si:H solar cells", Journal of Non-crystalline Solids: Volume 227-230: Part 2, pages 1295-1299 (May 1998). The plotted data were measured at various temperatures ranging from 150K (~–123° C.) to 300K (~27° C.). Since X-ray imaging systems typically operate at or around room-temperature, the topmost curve (300K) is the most relevant to the present discussion. Short-circuit current density under illumination is defined as the optical current ($I_{out}$) flowing through the p-i-n diode, divided by the cross-sectional area of the p-i-n diode, when the p-i-n diode is short-circuited by connecting its anode and cathode terminals together. In an ideal p-i-n diode, optical current under reverse bias (i.e. in photodetector mode) is the same as that under short circuit conditions. In practice, optical current may increase (often slightly) with reverse bias.

As previously described, in the disclosed detector of FIG. 9A, the p-i-n diode 340 operates in the solar-cell mode, whereas in conventional detectors, the p-i-n diodes operate in the photodetector mode. Typical a-Si:H p-i-n solar cells take about 5 μs to turn on after illumination, primarily because of the presence of deep traps in a-Si:H. (See FIG. 9C). Therefore, $V_{CHARGE}$ can be activated, e.g., about 10 μs after X-ray exposure, as shown in FIG. 9D.

When $V_{CHARGE}$ is turned on, $C_{ST}$ is connected in parallel to p-i-n diode 340; therefore $C_{ST}$ is either discharged (e.g., from point A1 in FIG. 9B) or charged (e.g., from point A2 in FIG. 9B) (depending on the pre-existing voltage on $C_{ST}$) to point B in FIG. 9B, which is the open-circuit-voltage ($V_{oc}$) corresponding to the optical current, $I_{opt}$, resulting from the illumination incident on the p-i-n diod 340. The voltage stored on $C_{ST}$ after charge or discharge is given by $V_{ST} \approx V_{oc} = n_0(KT/q).\ln(I_{opt}/I_{dark})$, where $n_0$ is the ideality factor of the p-i-n diode. The pre-existing voltage present on $C_{ST}$ may be a stray or residual voltage from operation in the past, or may be the open circuit voltage stored on $C_{ST}$ resulting from the incident illumination during the preceding frame time (which may be different from that of the current frame time if real-time imaging is being performed). When $C_{ST}$ is being discharged, the p-i-n diode 340 operates in the first quadrant (I>0 and V>0) of the I-V characteristics shown in FIG. 8B and the discharge time is of the order of the RC delay of the circuit which is given by $(R_{ON,CHARGE} + R_{S,diode}) \times C_{ST}$, where $R_{ON,CHARGE}$ is the ON-resistance of the charge transistor $T_{CHARGE}$, and is $R_{S,diode}$ the series resistance of the p-i-n diode 340. When $C_{ST}$ is being charged, the p-i-n diode 340 operates in the third quadrant (I<0 and V>0) of the I-V characteristics shown in FIG. 8B. Since the charge current is limited to $I_{opt}$, and open-circuit voltage ($V_{oc}$) is a sublinear (logarithmic) function of $I_{opt}$, the charge time is expected to have an approximately (to the first order) linear dependence on $I_{opt}$. More specifically, if we denote the charge current flowing to $C_{ST}$ at time t as i(t), and the voltage across $C_{ST}$ at time t as $v_{st}(t)$, where t=0 represent the time $T_{CHARGE}$ is switched on, we have:

$$i(t) \approx I_{opt} - I_{dark} \exp(q[v_{st}(t) + R_s i(t)]/n_0 KT),$$

where $R_S = R_{ON,CHARGE} + R_{S,diode}$. The charge current at t=0, referred to as i(0), can be calculated from the above equation numerically, for a known $v_{st}(0)$, the pre-existing voltage on $C_{ST}$. Next, i(0) can be used as the initial condition to solve the differential equation describing the charge circuit:

$$n_0 \frac{KT}{q} \ln\left(\frac{I_{opt} - i(t)}{I_{dark}}\right) = R_s i(t) + \frac{1}{C_{ST}} \int_0^t i(t)dt,$$

which has the following closed-form solution:

$$\frac{n_0 KT}{q I_{opt}} \ln\left(\frac{I_{opt} - i(t)}{I_{opt} - i(0)}\right) - \left(R_S + \frac{n_0 KT}{q I_{opt}}\right) \ln\left(\frac{i(t)}{i(0)}\right) = C_{ST} t.$$

The charge time is of the order of the effective RC delay of the circuit which may be approximated as $([V_{oc} - v_{st}(0)]/i(0) + R_S) C_{ST}$. Assuming that $R_S \ll [V_{oc} - v_{st}(0)]/i(0)$ and $I_{opt} \gg I_{dark}$, the charge time is to the first order proportional to $I_{opt}$. For example, in one embodiment, charge time is ~10 μs for 0.5 nA, ~0.1 ms for 50 pA, and ~1 ms for 5 pA. Typically 10% of $I_{opt,max}$ is used for lowest gray-scale level, so charge time of 0.1 ms is sufficient for most applications.

This X-ray exposure time ($t_{int}$) in FIG. 9D is at least 10× (ten times) lower (up to 100× lower) compared to conventional X-ray exposure, e.g., illustrated by FIG. 5.

Resetting the p-i-n diode 340 in FIG. 9A is optional, unless the frame time is short (e.g., <100 ms). Typical p-i-n a-Si:H solar cells take approximately 100 ms to completely turn off after illumination has turned off. As known in the art, this delayed turn-off is because of slow emission from deep traps. The detector circuit of FIG. 9A may include additional components and other variations in operation to the extent perceived by those skilled in the art may be considered. For example, an additional reset transistor may be used in parallel with $C_{ST}$ to reset any pre-existing voltage on $C_{ST}$ to zero before $T_{CHARGE}$ is switched on, and/or in some embodiments shorter charge times may be used to charge $C_{ST}$ to a fraction of $V_{oc}$ rather than $V_{oc}$. Resetting the p-i-n diode and/or using shorter charge times may be beneficial, e.g. for real-time imaging.

Figure 10:
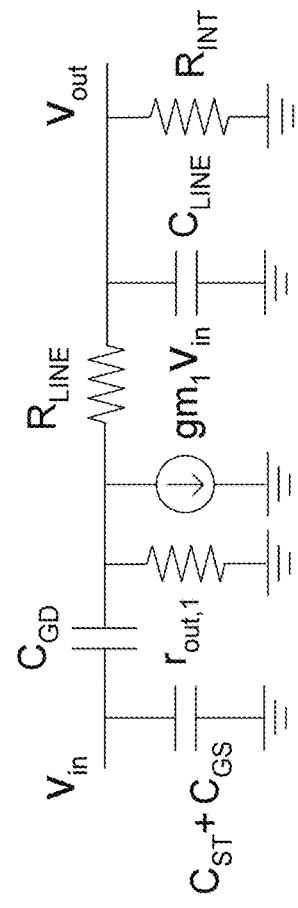
FIG. 10 is a small-signal circuit representation of a charge amplifier in an exemplary embodiment and is used for charge amplifier gain calculations.

Regarding charge amplifier gain for the active-matrix circuit 610, FIG. 10 is a small-signal circuit representation of a charge amplifier in an exemplary embodiment and is used for charge amplifier gain calculations. The disclosed charge amplifier from FIG. 6 is a common-source (CS) amplifier, where:

$$R_{LINE} = R_{ON,READ} + R_{DATA};$$

$$C_{LINE} = C_{DATA} + C_{FB};$$

$$r_{out,1} = (\partial I_{D1}/\partial V_{DS1})^{-1} = \text{small signal output resistance of } T_{AMP}; \text{ and}$$

$$R_{INT} = \text{Integrator Input Resistance.}$$

It is straightforward to derive the voltage gain, $A_V$ of the amplifier using Kirchhoff's voltage and current laws. The result is:

$$A_V = \frac{V_{out}}{V_{in}} = \frac{j\omega C_{GD} - gm_1}{(1/r_{out,1} + j\omega C_{GD})(1 + R_{LINE}/R_{INT} + j\omega R_{LINE}C_{LINE}) + (1/R_{INT} + j\omega C_{LINE})}.$$

For large $r_{out,1}$ and $C_{GD} \ll C_{LINE}$, $A_V$ can be approximated as:

$$A_V = \frac{V_{out}}{V_{in}} \approx \frac{(j\omega C_{GD} - gm_1) R_{INT}}{(1 + j\omega R_{INT} C_{LINE})(1 + j\omega C_{GD} R_{LINE})}.$$

For $(R_{INT} C_{LINE})^{-1} \ll \omega \ll (R_{LINE} C_{GD})^{-1} \ll (gm_1 C_{GD})^{-1}$, $A_V$ can be further approximated as:

$$A_V \approx -gm_1/j\omega C_{LINE}.$$

Small-signal charge gain may be defined as, $A_Q = A_V C_{FB}/C_{PIX}$. Note the small-signal charge gain is proportional to the large-signal (actual) charge gain given by $gm_1 t_{read}/C_{PIX}$, and therefore it is a suitable figure-of-merit. The effective pixel capacitance, $C_{PIX} \approx C_{ST} + C_{GS}(1 - A_{V,DC})C_{GD}$. The DC voltage gain ($A_V$ at ω=0) is as follows:

$$A_{V,DC} = -gm_1 r_{out,1} R_{INT}/(R_{LINE} + R_{INT} + r_{out,1}) \approx -gm_1 R_{INT}.$$

Figure 11:
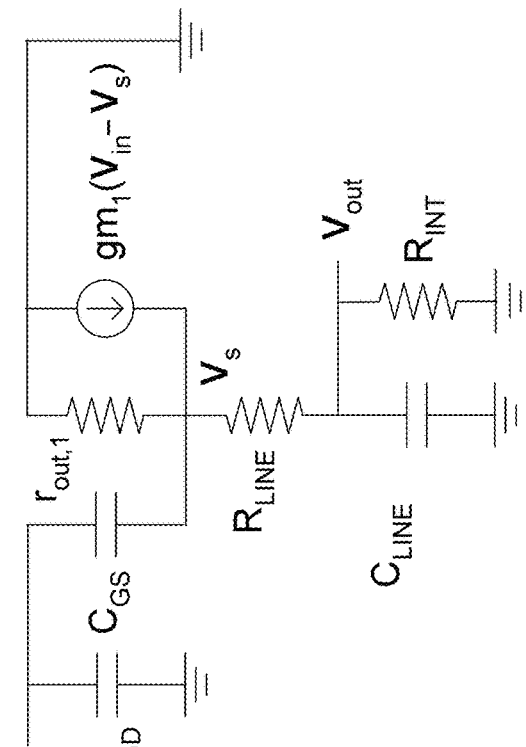
FIG. 11 is a small-signal circuit representation of a charge amplifier from the circuit of FIG. 7 and is used for charge amplifier gain calculations.

As for charge amplifier gain of conventional systems, FIG. 11 is a small-signal circuit representation of a charge amplifier from the circuit of FIG. 7. The charge amplifier in FIG. 7 is a source-follower (SF) amplifier, where:

$$R_{LINE} = R_{ON,READ} + R_{DATA};$$

$$C_{LINE} = C_{DATA} + C_{FB};$$

$r_{out,1} = (\partial I_{D1}/\partial V_{DS1})^{-1}$ = small signal output resistance of $T_{AMP}$; and $R_{INT}$ = Integrator Input Resistance.

The derived voltage gain, $A_V$ is the following:

$$A_V = \frac{V_{out}}{V_{in}} = \frac{(gm_1 + j\omega C_{GS})R_{INT}}{(1 + j\omega C_{LINE}R_{INT}) + (1/r_{out,1} + gm_1 + j\omega C_{GS})(R_{INT} + R_{LINE} + j\omega C_{LINE}R_{INT}R_{LINE})}.$$

For large $r_{out,1}$ and $C_{LINE} \gg C_{GS}$, $A_V$ can be approximated as:

$$A_V \approx \frac{(gm_1 + j\omega C_{GS})R_{INT}}{[1 + gm_1(R_{INT} + R_{LINE}) - \omega^2 C_{GS}C_{LINE}R_{INT}R_{LINE}] + j\omega R_{INT}C_{LINE}(1 + gm_1 R_{LINE})}.$$

For $\omega \ll gm_1/C_{GS}$, $A_V$ can be further approximated as:

$$A_V \approx \frac{gm_1 R_{INT}}{1 + gm_1(R_{INT} + R_{LINE}) + j\omega R_{INT}C_{LINE}(1 + gm_1 R_{LINE})}.$$

Small-signal charge gain may be defined as, $A_Q = A_V C_{FB}/C_{PIX}$, where the effective pixel capacitance is given by, $C_{PIX} \approx C_{PD} + C_{GD} + (1 - A_{V,DC})C_{GS} \approx C_{PD} + C_{GC} \approx C_{PD}$. The DC voltage gain is as follows:

$$A_{V,DC} = gm_1 R_{INT} r_{out,1}/[r_{out,1})(R_{INT} + R_{LINE})] \approx 1.$$

Exemplary charge gain calculations are as follows. Referring to FIGS. 12A, 12B, 12C, and 12D, which are graphs of charge gain versus frequency for $R_{INT}$=500 kΩ and $R_{LINE}$=500 kΩ in FIG. 12A, for $R_{INT}$=50 kΩ and $R_{LINE}$=500 kΩ in FIG. 12B, for $R_{INT}$=500 kΩ and $R_{LINE}$=50 kΩ in FIG. 12C, and for $R_{INT}$=50 kΩ and $R_{LINE}$=50 kΩ in FIG. 12D. These calculations are based on the following parameters:

gm$_1$=16 μA/V;
$C_{PD}$=1 pF;
$C_{ST}$=1 pF;
$C_{GS}$=100 fF;
$C_{GD}$=25 fF;
$C_{DATA}$100 pF;
$C_{FB}$=100 pF; and
$C_{LINE}$=$C_{FB}$+$C_{DATA}$=200 pF.

The gm $C_{GS}$ and $C_{GD}$ are based on assuming $T_{AMP}$ is an HJFET with W/L=20 μm/2 μm and drain current of 500 nA in subthreshold operation. Additionally, $R_{LINE}$=500KΩ & 50KΩ corresponding to a $T_{READ}$ HJFET with W/L=1 and 10 respectively (and assuming $R_{LINE}$ is dominated by $R_{ON,READ}$).

The disclosed charge amplifier (common-source) of FIG. 6 does not require a low line resistance ($R_{LINE}$) and therefore a low ON resistance for the READ transistor ($R_{ON,READ}$) to generate a high charge gain. This allows use of READ transistors with smaller channel width, thus reducing the pixel size and improving image resolution (particularly important for study of microcalcifications in the breast).

Additionally, the disclosed charge amplifier (common-source) does not require line integrators (e.g., readout circuit 670) with large input resistance ($R_{INT}$) to generate a high charge gain. As a result, line integrators may be implemented with relatively fewer transistors, simpler structures and/or lower-performance transistors including thin-film transistors compatible with large-area/flexible substrates, in some embodiments of the invention.

Figure 13:
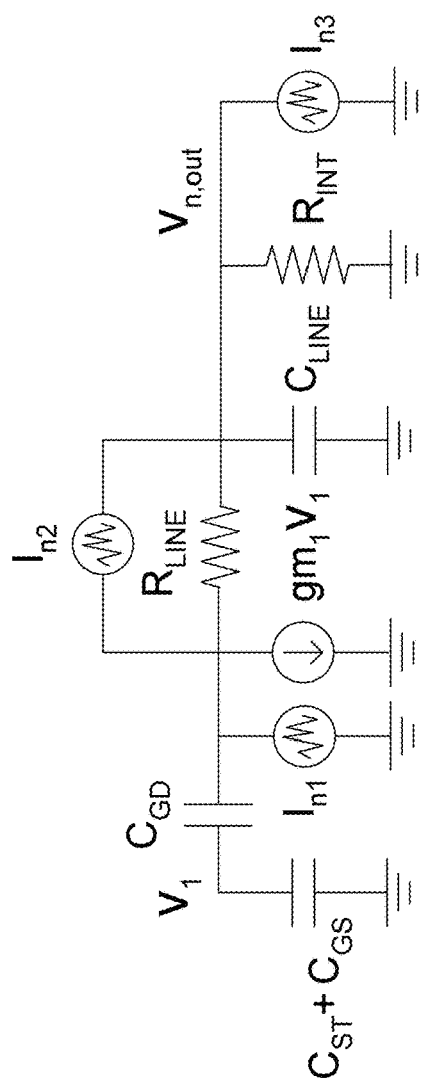
FIG. 13 is a small-signal circuit representation of a charge amplifier from FIG. 6 in an exemplary embodiment and is used for noise calculations.

Estimation may also be made of charge amplifier noise for the amplifier of the disclosed active-matrix circuit 610. FIG. 13 is a small-signal circuit representation of a charge amplifier in an exemplary embodiment and is used for noise calculations. For the disclosed charge amplifier, an input capacitance, $C_{in}$, and an equivalent transconductance, $gm_{eq}$, may be defined as follows:

$$C_{in} = \frac{C_{GD}(C_{GS} + C_{ST})}{C_{GD} + C_{GS} + C_{ST}}; \text{ and}$$

$$gm_{eq} = gm_1 \frac{C_{GD}}{C_{GD} + C_{GS} + C_{ST}}.$$

The output noise-voltage, $V_{n,out}$, can be derived using Kirchhoff's laws and is given by:

$$V_{n,out} = \frac{R_{INT}I_{n1} + R_{INT}R_{LINE}(gm_{eq} + sC_{in})I_{n2} + R_{INT}[1 + R_{LINE}(gm_{eq} + sC_{in})]I_{n3}}{1 + j\omega R_{INT}C_{LINE} + (gm_{eq} + j\omega C_{in})(R_{INT} + R_{LINE} + j\omega R_{INT}R_{LINE}C_{LINE})}.$$

If $\omega \ll gm_{eq}/C_{in}$, then $V_{n,out}$ can be approximated as:

$$V_{n,out} \approx \frac{\alpha_1 I_{n1} + \alpha_2 I_{n2} + \alpha_3 I_{n3}}{1 + j(\omega/\omega_{eq})}, \text{ where}$$

$$\omega_{eq} = 2\pi f_{eq} = \frac{1 + gm_{eq}(R_{INT} + R_{LINE})}{R_{INT}C_{LINE}(1 + gm_{eq}R_{LINE})}, \text{ and:}$$

$$\alpha_1 \approx \frac{R_{INT}}{1 + gm_{eq}(R_{INT} + R_{LINE})},$$

$$\alpha_2 \approx \frac{gm_{eq}R_{INT} + R_{LINE}}{1 + gm_{eq}(R_{INT} + R_{LINE})},$$

$$\alpha_3 \approx \frac{R_{INT}(1 + gm_{eq}R_{LINE})}{1 + gm_{eq}(R_{INT} + R_{LINE})}.$$

The output thermal noise variance, $\sigma_{th,out}^2$, is as follows:

$$\sigma_{th,out}^2 = \frac{\pi}{2} f_{eq}[\alpha_1^2(2/3)4KTgm_1 + \alpha_2^2(4KT/R_{LINE}) + \alpha_3^2(4KT/R_{INT})].$$

The input-referred thermal noise variance is given by:

$$\sigma_{th,in}^2 = \sigma_{th,out}^2/A_{V,DC}^2 = \sigma_{th,out}^2/(gm_1 R_{INT})^2.$$

Figure 14:
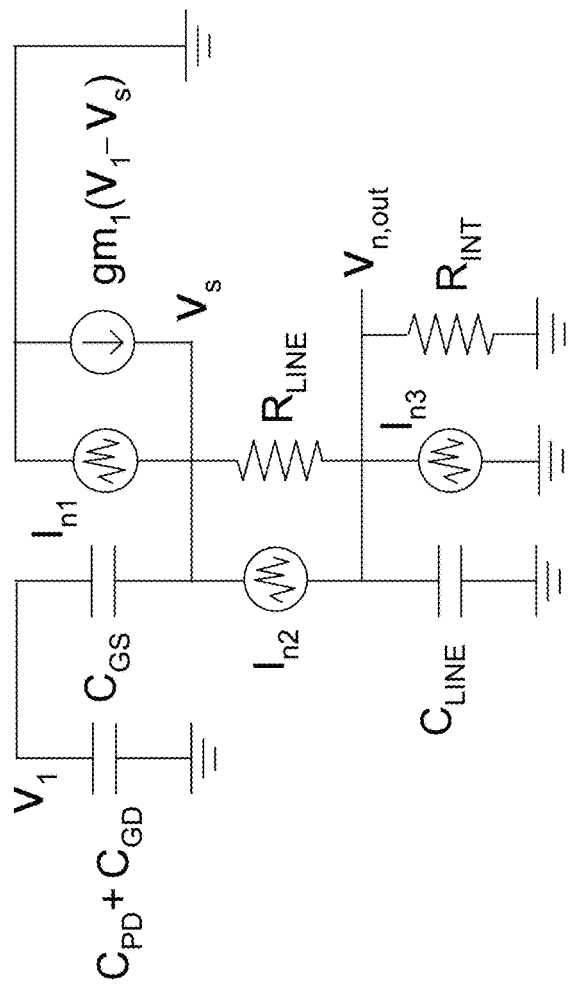
FIG. 14 is a small-signal circuit representation of a charge amplifier from the circuit of FIG. 7 and is used for noise calculations.

With respect to the conventional charge amplifier of the circuit in FIG. 7, FIG. 14 is a small-signal circuit representation of the charge amplifier from the circuit of FIG. 7 and is used for noise calculations. For the disclosed charge amplifier, an input capacitance, $C_{in}$, and an equivalent transconductance, $gm_{eq}$, may be defined as follows:

$$C_{in} = \frac{C_{GS}(C_{GD} + C_{PD})}{C_{GS} + C_{GD} + C_{PD}}; \text{ and}$$

$$gm_{eq} = gm_1 \frac{C_{GD} + C_{PD}}{C_{GS} + C_{GD} + C_{PD}}.$$

The voltage, $V_{n,out}$ is as follows:

$$V_{n,out} = \frac{R_{INT}I_{n1} + R_{INT}R_{LINE}(gm_{eq} + sC_{in})I_{n2} + R_{INT}[1 + R_{LINE}(gm_{eq} + sC_{in})]I_{n3}}{1 + j\omega R_{INT}C_{LINE} + (gm_{eq} + j\omega C_{in}) \cdot (R_{INT} + R_{LINE} + j\omega R_{INT}R_{LINE}C_{LINE})}.$$

If $\omega \ll gm_{eq}/C_{in}$, then $V_{n,out}$ can be approximated as:

$$V_{n,out} \approx \frac{\alpha_1 I_{n1} + \alpha_2 I_{n2} + \alpha_3 I_{n3}}{1 + j(\omega/\omega_{eq})}, \text{ where}$$

$$\omega_{eq} = 2\pi f_{eq} = \frac{1 + gm_{eq}(R_{INT} + R_{LINE})}{R_{INT}C_{LINE}(1 + gm_{eq}R_{LINE})}, \text{ and:}$$

$$\alpha_1 \approx \frac{R_{INT}}{1 + gm_{eq}(R_{INT} + R_{LINE})},$$

$$\alpha_2 \approx \frac{gm_{eq}R_{INT} + R_{LINE}}{1 + gm_{eq}(R_{INT} + R_{LINE})},$$

$$\alpha_3 \approx \frac{R_{INT}(1 + gm_{eq}R_{LINE})}{1 + gm_{eq}(R_{INT} + R_{LINE})}.$$

The output thermal noise variance, $\sigma_{th,out}^2$, is as follows:

$$\sigma_{th,out}^2 = \frac{\pi}{2} f_{eq}[\alpha_1^2(2/3)4KTgm_1 + \alpha_2^2(4KT/R_{LINE}) + \alpha_3^2(4KT/R_{INT})].$$

The input-referred thermal noise variance is given by:

$$\sigma_{th,in}^2 = \sigma_{th,out}^2/A_{V,DC}^2 \approx \sigma_{th,out}^2.$$

Exemplary charge amplifier noise calculations for the charge amplifier in active-matrix circuit 610 (the common-source, CS) and the charge amplifier in the conventional circuit in FIG. 7 (the source-follower, SF) were made. FIGS. 15A, 15B, 15C, and 15D are graphs of the first component, the second component, the third component, and the total input-referred thermal noise variance (in $\mu V/Hz^{1/2}$), respectively, versus resistance of the line ($R_{LINE}$) for input resistance ($R_{INT}$) of a line integrator of 500 k$\Omega$. The first, second and third components of the thermal noise variance are associated with the thermal noise of $T_{AMP}$ (M1), thermal noise of $R_{LINE}$ and thermal noise of $R_{INT}$, respectively, as described by the expressions above. FIGS. 16A, 16B, 16C, and 16D are graphs of the first, second and third component, and the total input-referred thermal noise variance (in $\mu V/Hz^{1/2}$), respectively, versus resistance of the line ($R_{LINE}$) for input resistance ($R_{INT}$) of a line integrator of 5 M$\Omega$. The following exemplary parameters were used for calculation in FIGS. 15A-15D, and 16A-16D: $gm_1$=16 $\mu$A/V, $C_{PD}$=$C_{ST}$=1 pF, $C_{GS}$=100 fF, $C_{GD}$=25 fF, $C_{DATA}$=$C_{FB}$=100 pF, $C_{LINE}$=$C_{FB}C_{DATA}$=200 pF. FIGS. 16E and 16F are graphs of the total input-referred thermal noise variance (in $\mu V/Hz^{1/2}$) versus resistance of the line ($R_{LINE}$) for input resistance ($R_{INT}$) of a line integrator of 5 $\Omega$g, and for CS (FIG. 16E) and SF (FIG. 16F), using the same parameters as FIGS. 15A-15D, and 16A-16D, except that a larger transconductance of $gm_1$=80 $\mu$A/V was used.

It can be seen that the common-source (CS) amplifier has a lower input-referred noise primarily due to higher gain as compared to the source-follower (SF) amplifier. The difference is particularly significant in FIGS. 16E and 16F, where $T_{AMP}$ has a larger transconductance value. This is because a higher transconductance results is a higher voltage gain in a CS amplifier, but the voltage gain of a SF amplifier cannot exceed 1 (unity) regardless of the transconductance value. A higher voltage gain translates into a lower input-referred noise, as explained earlier. FIG. 16F shows the input-referred noise for the SF amplifier to be around 6 $\mu V/Hz^{1/2}$, whereas the input-referred noise in FIG. 16E for the CS amplifier is less than 0.05 $\mu V/Hz^{1/2}$.

Since charge gain of the CS amplifier can be large even if W/L of M2 is small, more pixel area is available to increase W/L of M1 (and therefore $gm_1$) to significantly reduce the input-referred noise of the CS amplifier.

It should be noted that the flicker noise of the transistors was not included in the above estimation; however, it is straightforward to include the flicker noise if desired, as would be apparent to those skilled in the art, and the same advantages discussed above for the disclosed charge amplifier with respect to thermal noise would apply with respect to flicker noise as well. If double-sampling is used for the conventional charge amplifier or for the disclosed charge amplifier, as known, flicker noise is substantially eliminated but thermal noise is doubled. The advantages discussed above for the disclosed charge amplifier remain the same if double-sampling is used. An advantage of using HJFET devices as transistors is that HJFET has an inherently low flicker noise (since the gate of HJFET is comprised of a p-n hetero-junction rather than a gate dielectric) and in properly fabricated HJFET devices flicker noise is negligible (input-referred noise voltage and current below ~1 nV/Hz$^{1/2}$ and ~1 pA/Hz$^{1/2}$, respectively). Therefore, in charge amplifiers implemented with HJFET, flicker noise is negligible even without double-sampling. This prevents doubling the thermal noise (and noise from other sources) and also avoids other complications associated with double-sampling. This advantage of using HJFET is applicable both to conventional charge amplifiers and the disclosed charge amplifier.

Figure 17A:
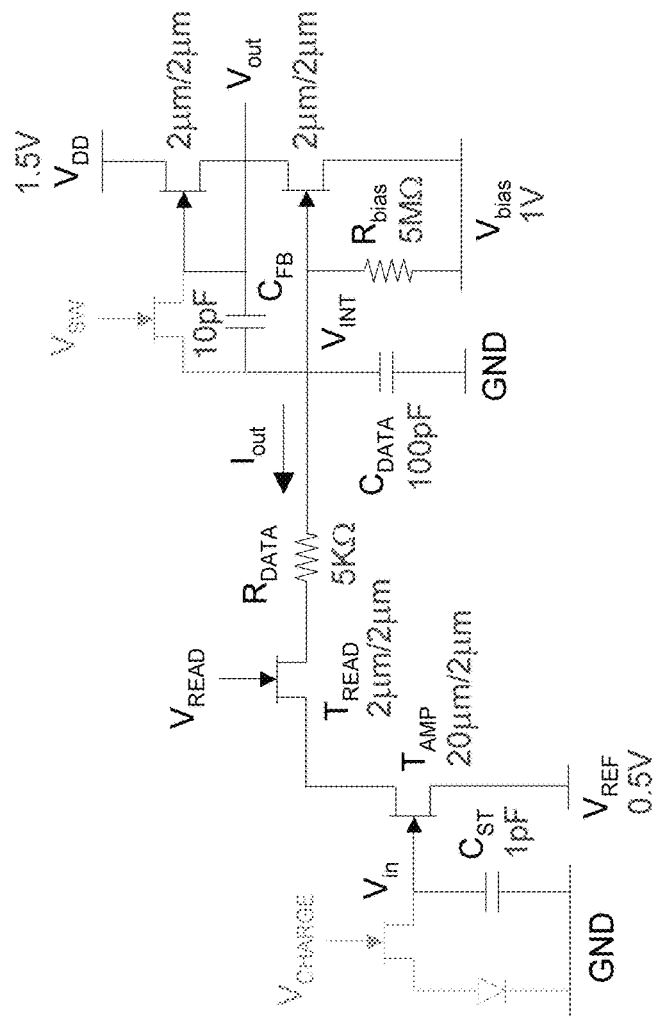
FIG. 17A is a circuit diagram of an exemplary embodiment, used for an HSPICE (an analog circuit simulator capable of performing transient, steady state, and frequency domain analyses) simulation example.
Figure 17B:
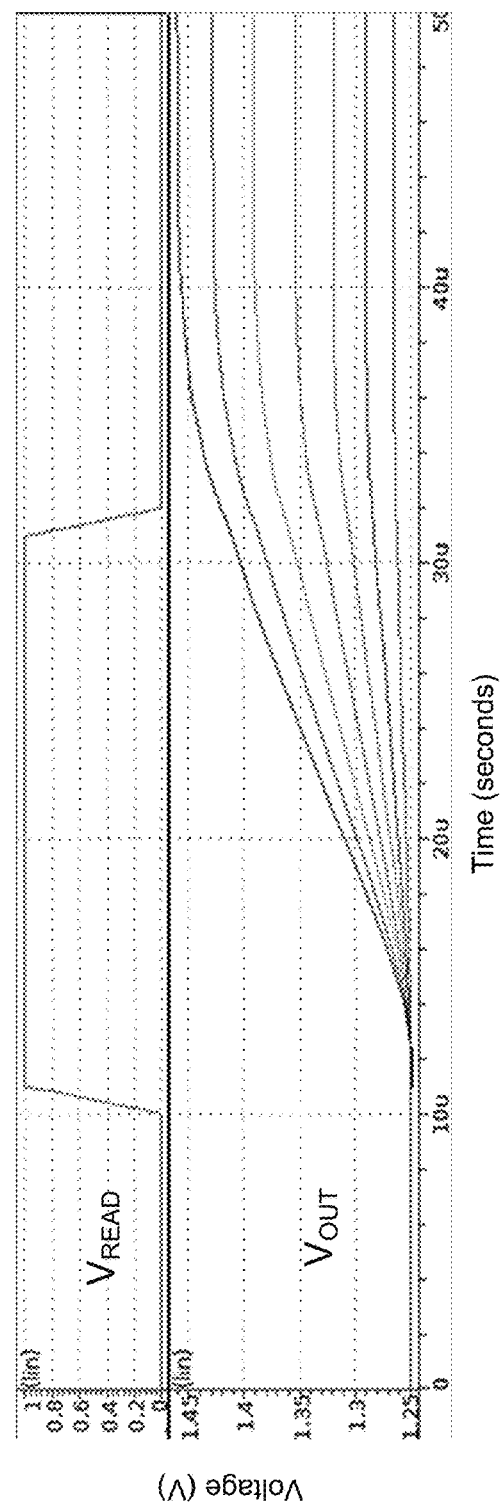
FIG. 17B is an exemplary output of the HSPICE simulation based on the circuit in FIG. 17A.

A transient simulation was performed using HSPICE, an analog circuit simulator capable of performing transient, steady state, and frequency domain analyses. FIG. 17A is a circuit diagram of an exemplary embodiment, used for this HSPICE simulation example, and FIG. 17B is an exemplary output of the HSPICE simulation based on the circuit in FIG. 17A. Transistor dimensions and other circuit parameters are given in the figure. The output voltage of the detector circuit (p-i-n diode, $T_{CHARGE}$ and $C_{ST}$) was used as the input voltage ($V_{in}$) to the charge amplifier circuit and the detector circuit itself was not included in the circuit simulation. Also, for simplicity, the initial (pre-existing) charge on feedback capacitor ($C_{FB}$) was set to zero at the start of simulation (t=0) and the switch transistor (SW) was not included in the simulation (because, in the absence of pre-existing charge, $C_{FB}$ does not need to be reset). Simulation results in FIG. 17B show output voltage ($V_{out}$) for input voltage, $V_{in}$ in the range of 0.4-0.5V (not shown in the plot), corresponding to optical current in the range of 0.5 nA-0.5 pA. The $V_{READ}$ in FIG. 17B is high for approximately 20 $\mu$s.

The simulated circuit has a voltage gain of about two and a charge gain of about 20, despite the small transistor dimensions and low power consumption. Maximum current flow through $T_{AMP}$ and $T_{READ}$ is about 0.5 $\mu$A. The standby current of the line integrator (which is biased in subthreshold regime) is about 50 nA. If desired, higher gain and/or higher integration speed may be achieved by larger W/L ratios and/or higher voltages.

The simulated transistors were HJFET devices, based on measurement results as described in reference to FIGS. 18A, 18B, and 18C. FIG. 18A is a structure of an underlapped thin-film HJFET used to provide parameters for the HSPICE simulation. FIG. 18B is a plot of the measured transfer characteristics for $V_{DS}$ of 0.1V and 0.9V on a graph of drain current (in amps, A) versus gate-to-source voltage (in volts, V) for the thin-film HJFET of FIG. 18A. The HJFET characterized in FIG. 18B has the following parameters: W=5 μm, $L_G$=2.5 μm, L=20 μm, $N_D$=$10^{18}$ cm$^{-3}$ and $t_{Si}$=32 nm. FIG. 18C illustrates contour lines for two pinch-off voltages ($V_P$=0.0V and −2.0V) as a function of thickness, $t_{Si}$ (in nm) and doping concentration, $N_D$ (in cm$^{-3}$), of a crystalline silicon (c-Si) layer of the thin-film HJFET of FIG. 18A. The contour lines indicate that for a given c-Si thickness ($t_{Si}$), the doping concentration of c-Si ($N_D$) can be adjusted to obtain a desired pinch-off voltage; or for a given c-Si doping concentration ($N_D$), the c-Si thickness ($t_{Si}$) may be adjusted to obtain a desired pinch-off voltage ($V_p$). For example, for the HJFET characterized in FIG. 18B, the ($t_{Si}$, $N_D$) point of (~32 nm, $10^{18}$ cm$^{-3}$) lies on the contour line for $V_p$=0.0V in FIG. 18C. The c-Si layer may be comprised of single-crystalline Si, also known as mono-crystalline Si (e.g. for the HJFET characterized in FIG. 18B) or poly-crystalline Si, including low-temperature poly-Si (LTPS) prepared by excimer laser crystallization (ELA) of amorphous Si. Note the basic device configuration of an HJFET is the same as that of a conventional junction field-effect transistor (JFET) except that the gate of an HJFET is comprised of an a-Si:H/c-Si p-n heterojunction whereas the gate of a conventional JFET is comprised of a c-Si/c-Si p-n homojunction (often referred to as a c-Si/c-Si p-n junction). The basic operation principles and electrical characteristics of an HJFET are therefore the same as that of a conventional JFET. It will be appreciated that a conventional JFET may also be used a transistor in the disclosed charge amplifier circuit. However, a thin-film HJFET might be preferred in some instances because it is compatible with large-area and/or flexible substrates.

FIG. 19 is a structure of a self-aligned thin-film HJFET that may be used as transistors in the active-matrix circuit 610. The self-aligned structure can be beneficial in reducing the device dimensions (for a given drive current) and also in reducing the gate overlap capacitance compared to the non-self-aligned HJFET structure.

Regardless of the structure of the HJFET, either from FIG. 18A or FIG. 19, the HJFET can be biased in the subthreshold regime to achieve high gain and high output impedance at low drive currents. In some embodiments, pinch-off voltage of the HJFET can be adjusted to be about zero (e.g. by adjusting the thickness and/or doping of the c-Si layer as explained with reference to FIG. 18C) and the gate bias can also be chosen to be about zero for following advantages:

(i) obtain highest possible gain at lowest operation voltage;

(ii) avoid need for an additional bias supply for applying negative bias to the HJFET gate; and (iii) eliminate standby power consumption by the gate bias network (by eliminating the need for a resistive voltage divider).

It should be noted that while the exemplary bias conditions mentioned above may be preferred in some embodiments, the feasible bias conditions are not limited to these bias conditions. In addition, the feasible transistor types and structures are not limited to the exemplary thin-film HJFET devices shown in FIGS. 18 and 19.

FIG. 20 shows a circuit diagram for a single-stage common-source amplifier comprised of a thin-film HJFET with a gate-to-source DC bias of zero volts, a load resistor, $R_D$, and a bias resistor $R_{bias}$. Further, $C_{in}$ represents an input capacitor, $V_{in}$ represents an input voltage and $V_{out}$ represents an output voltage. Assuming that the pinch-off voltage ($V_P$) of the HJFET is close to zero, the drain current of the HJFET may be expressed as $$I_D \approx I_{D0} \exp(qV_{GS}/nkT)[1-\exp(-qV_{DS}/kT)];$$

where $I_{D0}$ is the drain current at $V_{GS}$=0 and $V_{DS}$>>KT/q; and n is the ideality factor of the drain current in subthreshold (1≤n≤2). When $V_{DS}$>>KT/q the drain current approaches $I_D \approx I_{D0} \exp(qV_{GS}/nkT)$. The transconductance ($g_m$) and output resistance ($r_{out}$) of the HJFET are given by $$g_m = \partial I_D/\partial V_{GS} = qI_D/nkT; \text{ and}$$

$$r_{out} = (\partial I_D/\partial V_{DS})^{-1} = (kT/qI_D)\exp(qV_{DS}/kT).$$

Therefore, moderately high $g_m$ and very high $r_{out}$ may be achieved despite low $I_D$, thus enabling a high DC voltage gain. For example, consider the following values:

$V_{dd}$=1V;
n=1.2;
$I_D$=50 nA (W/L=1); and
$R_D$=10 MΩ

These values are chosen so that $V_{out,dc} \approx V_{dd}/2$. The above equations yield:

$$g_m \approx 1.6 \mu A/V; \text{ and}$$

|gain|≈$g_m R_D$=16. Note the amplifier portion of the integrator 670-2 shown in FIG. 6 is essentially the same as the single-stage common-source amplifier of FIG. 20, except that the passive load (resistor $R_D$) has been replaced with an active load (HJFET M3 biased at $V_{GS3}$=0).

While the equations above are explicitly written for HJFET, it will be appreciated by those skilled in the art that these equations are also applicable to MOSFETs with minor adjustments. In addition, while subthreshold operation is preferred, operation at or above threshold is also feasible and within the scope of this disclosure.

Turning to FIG. 21, this figure is a block diagram of a system 2100 for imaging, such as imaging breast tissue in a system 100. Such imaging may include a full field digital mammography (FFDM) system or a digital breast tomosynthesis (DBT) system, in accordance with an exemplary embodiment. The system 2100 comprises one or more control circuitries 2195, a measurement portion 190, and a user interface 2185. One exemplary measurement portion 190 is shown in FIG. 1, although the measurement portions are not limited to this style of DBT system. In the example of FIG. 21, the measurement portion 190 comprises a measurement structure 2140, which itself comprises an X-ray tube 120 and a detector 2110. The X-ray tube 120 and detector 2110 are attached to and form part of the measurement structure 2140 in an exemplary embodiment and the measurement structure 2140 may or may not rotate. If the measurement does rotate, the measurement structure 2140 could comprise the rotation structure 140 and rotating detector 110 of FIG. 1. In the exemplary embodiment of FIG. 1, the rotating detector 110 rotates because it is affixed to the rotation structure 140. Other configurations are possible, such as having the detector be fixed and the X-ray tube be rotated, or the X-ray tube be fixed and the detector be rotated. The detector 2110 (e.g., rotating detector 110) comprises an array 2190 of pixels 2160 of active-matrix circuits 610. The measurement portion 190 may also comprise other items for imaging, including imaging of breast tissue, such as a compression paddle and support plate, not shown in FIG. 21 but shown in FIG. 1.

The DBT system 100 also comprises a user interface 2185. The user interface 2185 may comprise, for instance, one or more displays (including touch screens), one or more keyboards, and one or more foot pedals. As an example, the display 2170 is an example of a user interface 2185, and the display 2170 comprises images 2810, which may be 2D images, 3D images, or both 2D and 3D images.

Each control circuitry 2195 comprises one or more memories 2120 and one or more processors 2150. Each processor is a general purpose or special purpose processor or other hardware, such an application specific integrated circuit. Program instructions 2130 are used to cause the measurement portion 190 to take measurements and determine output, which is then caused to be displayed on the one or more displays 2170 or other user interface. The program instructions 2130 may be part of the one or more memories 2120 as program instructions 2130-1, and the one or more processors 2150 would retrieve and execute the program instructions 2130-1, to cause the DBT system 100 to carry out operations to perform DBT on breast tissue. Alternatively or in addition, the program instructions 2130 may be part of the one or more processors 2150 (such as being circuitry inside the processor(s) 2120) and cause the system 2100 to carry out operations to perform measurements on breast tissue. It is noted that there may be multiple control circuitries 2120, such as if some or all of the user interface 2185 is separate from the measurement portion 190 but some or the user interface 2185 is also with the measurement portion 190.

With respect to the matrix 2190 of pixels 2160 of active-matrix circuits 610, the control circuitry 2195 is expected to cause the signals shown in, e.g., FIGS. 8 and 9D (e.g., and 17B) to cause the active-matrix circuits 610 to measure the charge created by their p-i-n diodes 340 in response to X-ray radiation caused by the X-ray tube 120. The matrix 2190 would comprise many such active-matrix circuits 610 as pixels 2160 in a matrix form and would have additional circuitry (not shown) to read out the pixels. An N×M matrix 2190 is shown in FIG. 21, with N rows and M columns of pixels 2160, and each pixel 2160 comprises an active-matrix circuit 610. The number N of rows may or may not be the same number M of columns.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following abbreviations that may be found in the specification and/or the drawing figures are defined as follows:

μs microseconds
2D two dimension(al)
3D three dimensions (or dimensional)
a—amorphous—(e.g., a-Si is amorphous silicon)
APS active pixel sensor
c—crystalline (e.g., c-Si is crystalline silicon)
C capacitance
cm centimeters
CMOS complementary metal-oxide-semiconductor
cs common source (also, CS)
DBT digital breast tomosynthesis
DC direct current
FFDM full field digital mammography
GND ground
HJFET heterojunction field-effect transistor
IC integrated circuit
LTPS low temperature polycrystalline silicon
MGD medium glandular dose
MOSFET metal oxide semiconductor field effect transistor
mGy milligray
opamp operational amplifier (also OpAmp or op-amp)
pF pico-Farad
R resistance
SF source-follower
T transistor
TFT thin-film transistor
V volts

What is claimed is:

1. An imaging system, comprising:
a detector comprising a matrix of pixels, the matrix comprising N rows and M columns of pixels, each of a plurality of the pixels comprising:
a circuit comprising:
a p-i-n diode having a cathode of the p-i-n diode is coupled to a cathode bias voltage or ground;
a charge transistor having a first source/drain terminal coupled to an anode of the p-i-n diode and a second source/drain terminal to the cathode of the p-i-n diode;
a storage capacitor having a first terminal coupled to a second source/drain terminal of the charge transistor and a second terminal coupled to the cathode of the p-i-n diode;
an amplification transistor having a gate terminal coupled to the first terminal of the storage capacitor and a first source/drain terminal coupled to a reference voltage in operation;
a read transistor having a first source/drain terminal coupled to a second source/drain terminal of the amplification transistor;
a data line having a first terminal coupled to a second source/drain terminal of the read transistor; and
a readout circuit coupled to a second terminal of the data line and configured to provide in operation an output voltage corresponding to charge on the storage capacitor caused by interaction between the p-i-n diode and light.

2. The imaging system of claim 1, wherein:
each of the plurality of the pixels comprises a scintillator spaced apart from but aligned at least in part with the p-i-n diode;
the imaging system further comprises an X-ray tube, wherein the X-ray tube and detector are arranged so that an X-ray beam formed by the X-ray tube will illuminate at least a portion of the detector, the scintillators in the matrix will create visible light from the X-ray beam, and the visible light is directed to surfaces of individual ones of the p-i-n diodes in the matrix.

3. The imaging system of claim 1, wherein the reference voltage is chosen such that direction of current flow is from the readout circuit towards the amplification transistor and therefore a second source/drain terminal of the amplification transistor is a functional drain of the amplification transistor.

4. The imaging system of claim 1, wherein the reference voltage is chosen such that the amplification transistor is biased in a subthreshold regime.

5. The imaging system of claim 2, wherein the imaging system comprises one of a full field digital mammography system or a digital breast tomosynthesis system.

6. The imaging system of claim 5, further comprising a compression paddle and a support plate for containing breast tissue therebetween, and the compression paddle and support plate are arranged to that at least part of the X-ray beam passes through the breast tissue and illuminates the detector.

7. The imaging system of claim 5, wherein the system comprises is a digital breast tomosynthesis system and wherein the system further comprises:

a rotation structure comprising the detector and the X-ray tube, the rotation structure is configured to be able to rotate over an angular range;

at least one control circuitry, the at least one control circuitry configured to cause a measurement to be made by causing the X-ray tube to form the X-ray beam and causing the detector to produce an output, wherein the at least one control circuitry is configured to cause rotation of the rotation structure at least some non-zero portion of the angular range and to cause multiple measurements to be made over the non-zero portion of the angular range.

8. The imaging system of claim 7, wherein the at least one control circuitry comprises at least one memory comprising program instructions and comprises at least one processor, wherein the at least one processor, in response to retrieval and execution of the program instructions, causes the apparatus to perform at least the measurement.

9. The imaging system of claim 1, wherein the readout circuit comprises:

a feedback capacitor having a first terminal coupled to the second terminal of the data line;

a switch transistor in parallel with the feedback capacitor, having a first terminal coupled to the second terminal of the data line and having a second terminal coupled to a second terminal of the feedback capacitor;

a bias resistor having a first terminal coupled to the second terminal of the data line and a second terminal coupled to a source bias voltage in operation;

an active-load transistor having a gate terminal coupled to a source/drain terminal or a gate bias voltage, having a first source/drain terminal coupled to a supply voltage in operation, and having a source/drain second terminal coupled to an output terminal; and a common-source transistor having a gate terminal coupled to the second terminal of the data line, having a first source/drain terminal coupled to the output terminal, and having a source/drain second terminal coupled to the source bias voltage in operation.

* * * * *